(12) United States Patent
Sorgenfrei et al.

(10) Patent No.: US 12,213,765 B2
(45) Date of Patent: *Feb. 4, 2025

(54) PHOTODETECTOR CALIBRATION OF AN OPTICAL MEASUREMENT SYSTEM

(71) Applicant: HI LLC, Los Angeles, CA (US)

(72) Inventors: Sebastian Sorgenfrei, Playa Vista, CA (US); Ryan Field, Culver City, CA (US); Bruno Do Valle, Brighton, MA (US); Isai Olvera, South Portland, ME (US); Jacob Dahle, Arlington, MA (US); Husam Katnani, Braintree, MA (US)

(73) Assignee: HI LLC, Culver City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/524,743

(22) Filed: Nov. 30, 2023

(65) Prior Publication Data

US 2024/0099587 A1   Mar. 28, 2024

Related U.S. Application Data

(63) Continuation of application No. 17/202,668, filed on Mar. 16, 2021, now Pat. No. 11,903,676.

(Continued)

(51) Int. Cl.
*A61B 5/00* (2006.01)

(52) U.S. Cl.
CPC .......... *A61B 5/0082* (2013.01); *A61B 5/4064* (2013.01); *A61B 5/6803* (2013.01);
(Continued)

(58) Field of Classification Search
CPC ... A61B 5/0082; A61B 5/4064; A61B 5/6803; A61B 5/7217; A61B 2560/0223; A61B 2560/0443; A61B 2562/046
See application file for complete search history.

(56) References Cited

U.S. PATENT DOCUMENTS 5,853,370 A   12/1998   Chance et al.
5,924,982 A   7/1999   Chin
(Continued)

OTHER PUBLICATIONS

Alayed, et al., Characterization of a Time-Resolved Diffuse Optical Spectroscopy Prototype Using Low-Cost, Compact Single Photon Avalanche Detectors for Tissue Optics Applications, Sensors 2018, 18, 3680; doi:10.3390/s18113680, Oct. 29, 2018.

(Continued)

*Primary Examiner* — Sean A Frith
(74) *Attorney, Agent, or Firm* — ALG Intellectual Property, LLC

(57) ABSTRACT

An illustrative optical measurement system includes a light source configured to emit light directed at a target, an array of photodetectors configured to detect photons of the light after the light is scattered by the target, and a processing unit configured to measure a noise level of a photodetector included in the array of photodetectors, the noise level comprising a dark count rate that measures a dark count divided by a time period, determine that the noise level meets a predetermined threshold comprising a dark count rate threshold, and prevent, based on the determining that the noise level meets the predetermined threshold, an output of the photodetector from being used in generating a histogram based on a temporal distribution of photons detected by the array of photodetectors, the preventing comprising switching the output to a monitoring circuit that monitors a characteristic of the optical measurement system separate from the photodetector.

20 Claims, 21 Drawing Sheets

Related U.S. Application Data

(60) Provisional application No. 63/070,123, filed on Aug. 25, 2020, provisional application No. 62/992,536, filed on Mar. 20, 2020.

(52) U.S. Cl.
CPC .... *A61B 5/7217* (2013.01); *A61B 2560/0223* (2013.01); *A61B 2560/0443* (2013.01); *A61B 2562/046* (2013.01)

(56) References Cited

U.S. PATENT DOCUMENTS

| | | |
|---|---|---|
| 6,195,580 B1 | 2/2001 | Grable |
| 6,240,309 B1 | 5/2001 | Yamashita et al. |
| 6,384,663 B2 | 5/2002 | Cova et al. |
| 6,640,133 B2 | 10/2003 | Yamashita et al. |
| 6,683,294 B1 | 1/2004 | Herbert et al. |
| 7,356,365 B2 | 4/2008 | Schurman |
| 7,547,872 B2 | 6/2009 | Niclass et al. |
| 7,774,047 B2 | 8/2010 | Yamashita et al. |
| 7,888,973 B1 | 2/2011 | Rezzi et al. |
| 8,026,471 B2 | 9/2011 | Itzler |
| 8,078,250 B2 | 12/2011 | Chen et al. |
| 8,082,015 B2 | 12/2011 | Yodh et al. |
| 8,269,563 B2 | 9/2012 | Ballantyne |
| 8,518,029 B2 | 8/2013 | Birmingham et al. |
| 8,633,431 B2 | 1/2014 | Kim |
| 8,817,257 B2 | 8/2014 | Herve |
| 9,058,081 B2 | 6/2015 | Baxter |
| 9,076,707 B2 | 7/2015 | Harmon |
| 9,131,861 B2 | 9/2015 | Ince et al. |
| 9,316,735 B2 | 4/2016 | Baxter |
| 9,401,448 B2 | 7/2016 | Bienfang et al. |
| 9,419,635 B2 | 8/2016 | Kumar et al. |
| 9,442,201 B2 | 9/2016 | Schmand et al. |
| 9,529,079 B1 | 12/2016 | Droz et al. |
| 9,554,738 B1 | 1/2017 | Gulati et al. |
| 9,574,936 B2 | 2/2017 | Heinonen |
| 9,946,344 B2 | 4/2018 | Ayaz et al. |
| D817,553 S | 5/2018 | Aaskov et al. |
| 9,983,670 B2 | 5/2018 | Coleman et al. |
| D825,112 S | 8/2018 | Saez |
| 10,158,038 B1 | 12/2018 | Do et al. |
| 10,340,408 B1 | 7/2019 | Katnani et al. |
| 10,424,683 B1 | 9/2019 | Valle et al. |
| 10,515,993 B2 | 12/2019 | Field et al. |
| 10,697,829 B2 | 6/2020 | Delic |
| 10,772,561 B2 | 9/2020 | Donaldson |
| 10,809,796 B2 | 10/2020 | Armstrong-Muntner et al. |
| 10,912,504 B2 | 2/2021 | Nakaji et al. |
| 11,006,876 B2 | 5/2021 | Johnson et al. |
| 11,006,878 B2 | 5/2021 | Johnson et al. |
| 11,213,245 B2 | 1/2022 | Horstmeyer et al. |
| 11,903,676 B2* | 2/2024 | Sorgenfrei ............ A61B 5/0059 |
| 2005/0059869 A1 | 3/2005 | Scharf et al. |
| 2007/0083097 A1 | 4/2007 | Fujiwara et al. |
| 2009/0012402 A1 | 1/2009 | Mintz et al. |
| 2010/0007413 A1 | 1/2010 | Herleikson et al. |
| 2011/0208675 A1 | 8/2011 | Shoureshi et al. |
| 2012/0016635 A1 | 1/2012 | Brodsky et al. |
| 2013/0015331 A1* | 1/2013 | Birk .................... G01J 1/18 250/208.2 |
| 2013/0090541 A1* | 4/2013 | MacFarlane ......... A61B 5/0042 600/328 |
| 2013/0300838 A1 | 11/2013 | Borowski et al. |
| 2013/0342835 A1 | 12/2013 | Blacksberg |
| 2014/0191115 A1 | 7/2014 | Webster et al. |
| 2014/0217264 A1* | 8/2014 | Shepard ............ G01N 21/6408 257/438 |
| 2014/0275891 A1 | 9/2014 | Muehlemann et al. |
| 2015/0038811 A1 | 2/2015 | Asaka et al. |
| 2015/0041625 A1 | 2/2015 | Dutton et al. |
| 2015/0054111 A1 | 2/2015 | Niclass et al. |
| 2015/0077279 A1 | 3/2015 | Song et al. |
| 2015/0150505 A1 | 6/2015 | Kaskoun et al. |
| 2015/0327777 A1 | 11/2015 | Kostic et al. |
| 2015/0364635 A1* | 12/2015 | Bodlovic ............ H01L 31/024 250/214.1 |
| 2016/0057369 A1 | 2/2016 | Wolfe et al. |
| 2016/0182902 A1 | 6/2016 | Guo et al. |
| 2016/0296168 A1 | 10/2016 | Abreu |
| 2016/0349368 A1 | 12/2016 | Stutz et al. |
| 2017/0030769 A1 | 2/2017 | Clemens et al. |
| 2017/0052065 A1 | 2/2017 | Sharma et al. |
| 2017/0176596 A1 | 6/2017 | Shpunt et al. |
| 2017/0179173 A1 | 6/2017 | Mandai et al. |
| 2017/0202518 A1 | 7/2017 | Furman et al. |
| 2017/0281086 A1 | 10/2017 | Donaldson |
| 2017/0363467 A1 | 12/2017 | Clemens et al. |
| 2017/0367650 A1 | 12/2017 | Wallois et al. |
| 2018/0014741 A1 | 1/2018 | Chou |
| 2018/0027196 A1 | 1/2018 | Yang et al. |
| 2018/0033751 A1 | 2/2018 | Ban et al. |
| 2018/0039053 A1 | 2/2018 | Kremer et al. |
| 2018/0066986 A1 | 3/2018 | Kasai et al. |
| 2018/0070830 A1 | 3/2018 | Sutin et al. |
| 2018/0070831 A1 | 3/2018 | Sutin et al. |
| 2018/0089848 A1 | 3/2018 | Yang et al. |
| 2018/0090536 A1 | 3/2018 | Mandai et al. |
| 2018/0120152 A1 | 5/2018 | Leonardo |
| 2018/0180473 A1 | 6/2018 | Clemens et al. |
| 2018/0192931 A1 | 7/2018 | Linden et al. |
| 2019/0113385 A1 | 4/2019 | Fukuchi |
| 2019/0120975 A1 | 4/2019 | Ouvrier-Buffet |
| 2019/0175068 A1 | 6/2019 | Everdell |
| 2019/0355861 A1 | 11/2019 | Katnani et al. |
| 2019/0363210 A1 | 11/2019 | Valle et al. |
| 2019/0388018 A1 | 12/2019 | Horstmeyer et al. |
| 2020/0060542 A1 | 2/2020 | Alford et al. |
| 2020/0116838 A1 | 4/2020 | Erdogan et al. |
| 2020/0196932 A1 | 6/2020 | Johnson et al. |
| 2020/0253479 A1 | 8/2020 | Nurmikko |
| 2020/0315510 A1 | 10/2020 | Johnson et al. |
| 2020/0337624 A1 | 10/2020 | Johnson et al. |
| 2020/0379095 A1 | 12/2020 | Kappel et al. |
| 2020/0390358 A1 | 12/2020 | Johnson et al. |
| 2021/0186138 A1 | 6/2021 | Bartels et al. |

OTHER PUBLICATIONS

Ban, et al., Kernel Flow: a high channel count scalable TD-fNIRS system, https://www.spiedigitallibrary.org/conference-proceedings-of-spie Proc. of SPIE vol. 11663, 116630B doi: 10.1117/12.2582888, Mar. 5, 2021.

Ban, et al., Kernel Flow: a high channel count scalable time-domain functional near-infrared spectroscopy system, https://www.spiedigitallibrary.org/journals/Journal-of-Biomedical-Optics on Jan. 18, 2022.

Contini, et al., Photon migration through a turbid slab described by a model based on diffusion approximation. I. Theory, Appl. Opt. 36(19), 4587 (1997).

Di Sieno, et al., Probe-hosted large area silicon photomultiplier and high-throughput timing electronics for enhanced performance time-domain functional near-infrared spectroscopy, Biomed. Opt. Express 11(11), 6389 (2020).

Fishburn, et al., Temporal Derivative Distribution Repair (TDDR): A motion correction method for fNIRS, Neuroimage. Jan. 1, 2019; 184: 171-179. doi:10.1016/j.neuroimage.2018.09.025.

Huppert, et al., HomER: a review of time-series analysis methods for near-infrared spectroscopy of the brain, Appl. Opt. 48(10), D280 (2009).

Kienle, et al., Improved solutions of the steady-state and the time-resolved diffusion equations for reflectance from a semi-infinite turbid medium, J. Opt. Soc. Am. A 14(1), 246 (1997).

Konugolu, et al., Broadband (600-1350 nm) Time-Resolved Diffuse Optical Spectrometer for Clinical Use, IEEE Journal of Selected Topics in Quantum Electronics, vol. 22, No. 3, May/Jun. 2016.

Lacerenza, et al., Wearable and wireless time-domain near-infrared spectroscopy system for brain and muscle hemodynamic monitoring, Biomed. Opt. Express 11(10), 5934 (2020).

(56) References Cited

OTHER PUBLICATIONS

Lange, et al., Clinical Brain Monitoring with Time Domain Nirs: A Review and Future Perspectives, Applied Sciences 9(8), 1612 (2019).

Lange, et al., MAESTROS: A Multiwavelength Time-Domain NIRS System to Monitor Changes in Oxygenation and Oxidation State of Cytochrome-C-Oxidase, IEEE J. Select. Topics Quantum Electron. 25(1), 1-12 (2019).

Martelli, et al., Optimal estimation reconstruction of the optical properties of a two-layered tissue phantom from time-resolved single-distance measurements, Journal of Biomedical Optics 20(11), 115001 (Nov. 2015).

Mora, et al., Fast silicon photomultiplier improves signal harvesting and reduces complexity in time-domain diffuse optics, Opt. Express 23(11), 13937 (2015).

Pifferi, et al., Performance assessment of photon migration instruments: the MEDPHOT protocol, Applied Optics, 44 (11), 2104-2114, 2005.

Prahl, Optical Absorption of Hemoglobin, http://omlc.ogi.edu/spectra/hemoglobin/index.html, 1999.

Re, et al., Multi-channel medical device for time domain functional near infrared spectroscopy based on wavelength space multiplexing, Biomed. Opt. Express 4(10), 2231 (2013).

Renna, et al., Eight-Wavelength, Dual Detection Channel Instrument for Near-Infrared Time-Resolved Diffuse Optical Spectroscopy, IEEE J. Select. Topics Quantum Electron. 25(1), 1-11 (2019).

Torricelli, et al., Time domain functional NIRS imaging for human brain mapping, NeuroImage 85, 28-50 (2014).

Wabnitz, et al., Depth-selective data analysis for time-domain fNIRS: moments vs. time windows, Biomed. Opt. Express 11(8), 4224 (2020).

Wabnitz, et al., Performance assessment of time-domain optical brain imagers, part 1: basic instrumental performance protocol, Journal of Biomedical Optics 19(8), 086010 (Aug. 2014).

Wabnitz, et al., Performance assessment of time-domain optical brain imagers, part 2: nEUROPt protocol, Journal of Biomedical Optics 19(8), 086012 (Aug. 2014).

Wojtkiewicz, et al., Self-calibrating time-resolved near infrared spectroscopy, Biomed. Opt. Express 10(5), 2657 (2019).

Zucchelli, et al., Method for the discrimination of superficial and deep absorption variations by time domain fNIRS, 2013 OSA Dec. 1, 2013 | vol. 4, No. 12 | DOI:10.1364/BOE.4.002893 | Biomedical Optics Express 2893, 2013.

"What are the advantages of multiplexing," Blog, FiberWDM, Mar. 28, 2023. Retrieved on May 9, 2014 from https://www.fiberwdm.com/blog/what-are-the-advantages-of-multiplexing_b101.

Blair, Seraphine. "Multiplexing in modern communication: what it is & advantages," Blog, JAK Electronics, Mar. 12, 2024. Retrieved on May 9, 2024 from https://www.jakelectronics.com/blog/multiplexing.

Nandalal, et al., "Multiplexing," IntechOpen, Sep. 4, 2019. Retrieved on May 9, 2014 from https://www.jakelectronics.com/blog/multiplexing.

* cited by examiner

PHOTODETECTOR CALIBRATION OF AN OPTICAL MEASUREMENT SYSTEM

RELATED APPLICATIONS

The present application is a continuation of U.S. patent application Ser. No. 17/202,668, filed Mar. 16, 2021, which claims priority under 35 U.S.C. § 119(e) to U.S. Provisional Patent Application No. 62/992,536, filed Mar. 20, 2020, and to U.S. Provisional Patent Application No. 63/070,123, filed Aug. 25, 2020. These applications are incorporated herein by reference in their respective entireties.

BACKGROUND INFORMATION

Detecting neural activity in the brain (or any other turbid medium) is useful for medical diagnostics, imaging, neuro-engineering, brain-computer interfacing, and a variety of other diagnostic and consumer-related applications. For example, it may be desirable to detect neural activity in the brain of a user to determine if a particular region of the brain has been impacted by reduced blood irrigation, a hemorrhage, or any other type of damage. As another example, it may be desirable to detect neural activity in the brain of a user and computationally decode the detected neural activity into commands that can be used to control various types of consumer electronics (e.g., by controlling a cursor on a computer screen, changing channels on a television, turning lights on, etc.).

Neural activity and other attributes of the brain may be determined or inferred by measuring responses of tissue within the brain to light pulses. One technique to measure such responses is time-correlated single-photon counting (TCSPC). Time-correlated single-photon counting detects single photons and measures a time of arrival of the photons with respect to a reference signal (e.g., a light source). By repeating the light pulses, TCSPC may accumulate a sufficient number of photon events to statistically determine a histogram representing the distribution of detected photons. Based on the histogram of photon distribution, the response of tissue to light pulses may be determined in order to study the detected neural activity and/or other attributes of the brain.

A photodetector capable of detecting a single photon (i.e., a single particle of optical energy) is an example of a non-invasive detector that can be used in an optical measurement system to detect neural activity within the brain. An exemplary photodetector is implemented by a semiconductor-based single-photon avalanche diode (SPAD), which is capable of capturing individual photons with very high time-of-arrival resolution (a few tens of picoseconds).

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

In accordance with the systems, circuits, and methods described herein, an optical measurement system may include one or more arrays of photodetectors. A noise level for each photodetector of the one or more arrays of photodetectors may be measured and compared to a predetermined threshold. Outputs of photodetectors that are determined to meet the predetermined threshold (i.e., relatively noisy photodetectors) may be prevented from being included when generating histograms that represent a temporal distribution of photons detected by the one or more arrays of photodetectors.

Systems, circuits, and methods described herein may include a plurality of counting circuits that include a respective counting circuit for each photodetector. The counting circuits may be used to measure the noise levels of the photodetectors concurrently.

Photodetectors that are determined to be noisy may be prevented from being included in generating histograms in a variety of manners. For example, such photodetectors may be disabled. As another example, outputs of such photodetectors may be redirected to a monitoring circuit that monitors characteristics of the optical measurement system.

By preventing outputs of noisy photodetectors from being used in generating histograms, systems, circuits, and methods described herein may allow for more accurate and/or more sensitive optical measurement systems than optical measurement systems that use outputs of all the photodetectors in generating histograms. Further, in situations where the outputs of noisy photodetectors are switched to a monitoring circuit, the noisy photodetectors may provide additional benefits associated with the optical measurement system, as will be described in more detail herein.

These and other advantages and benefits of the present systems, circuits, and methods are described more fully herein.

Figure 1:
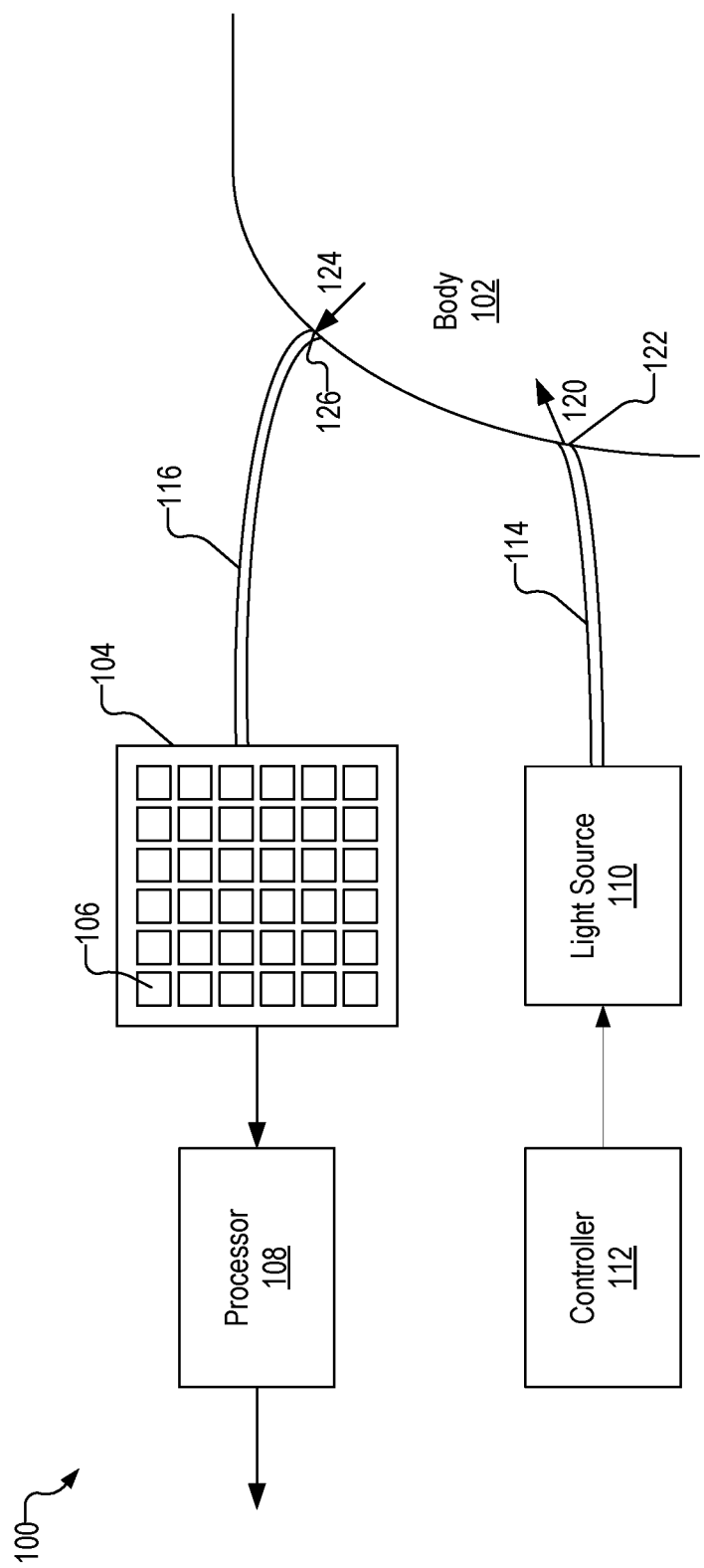
FIG. 1 shows an exemplary optical measurement system.

FIG. 1 shows an exemplary optical measurement system 100 configured to perform an optical measurement operation with respect to a body 102. Optical measurement system 100 may, in some examples, be portable and/or wearable by a user. Optical measurement systems that may be used in connection with the embodiments described herein are described more fully in U.S. patent application Ser. No. 17/176,315, filed Feb. 16, 2021; U.S. patent application Ser.

No. 17/176,309, filed Feb. 16, 2021; U.S. patent application Ser. No. 17/176,460, filed Feb. 16, 2021; U.S. patent application Ser. No. 17/176,470, filed Feb. 16, 2021; U.S. patent application Ser. No. 17/176,487, filed Feb. 16, 2021; U.S. patent application Ser. No. 17/176,539, filed Feb. 16, 2021; U.S. patent application Ser. No. 17/176,560, filed Feb. 16, 2021; and U.S. patent application Ser. No. 17/176,466, filed Feb. 16, 2021, which applications are incorporated herein by reference in their entirety.

In some examples, optical measurement operations performed by optical measurement system 100 are associated with a time domain-based optical measurement technique. Example time domain-based optical measurement techniques include, but are not limited to, TCSPC, time domain near infrared spectroscopy (TD-NIRS), time domain diffusive correlation spectroscopy (TD-DCS), and time domain Digital Optical Tomography (TD-DOT).

As shown, optical measurement system 100 includes a detector 104 that includes a plurality of individual photodetectors (e.g., photodetector 106), a processor 108 coupled to detector 104, a light source 110, a controller 112, and optical conduits 114 and 116 (e.g., light pipes). However, one or more of these components may not, in certain embodiments, be considered to be a part of optical measurement system 100. For example, in implementations where optical measurement system 100 is wearable by a user, processor 108 and/or controller 112 may in some embodiments be separate from optical measurement system 100 and not configured to be worn by the user.

Detector 104 may include any number of photodetectors 106 as may serve a particular implementation, such as 2" photodetectors (e.g., 256, 512, . . . , 16384, etc.), where n is an integer greater than or equal to one (e.g., 4, 5, 8, 10, 11, 14, etc.). Photodetectors 106 may be arranged in any suitable manner.

Photodetectors 106 may each be implemented by any suitable circuit configured to detect individual photons of light incident upon photodetectors 106. For example, each photodetector 106 may be implemented by a single photon avalanche diode (SPAD) circuit and/or other circuitry as may serve a particular implementation.

Processor 108 may be implemented by one or more physical processing (e.g., computing) devices. In some examples, processor 108 may execute instructions (e.g., software) configured to perform one or more of the operations described herein.

Light source 110 may be implemented by any suitable component configured to generate and emit light. For example, light source 110 may be implemented by one or more laser diodes, distributed feedback (DFB) lasers, super luminescent diodes (SLDs), light emitting diodes (LEDs), diode-pumped solid-state (DPSS) lasers, super luminescent light emitting diodes (sLEDs), vertical-cavity surface-emitting lasers (VCSELs), titanium sapphire lasers, micro light emitting diodes (mLEDs), and/or any other suitable laser or light source. In some examples, the light emitted by light source 110 is high coherence light (e.g., light that has a coherence length of at least 5 centimeters) at a predetermined center wavelength.

Light source 110 is controlled by controller 112, which may be implemented by any suitable computing device (e.g., processor 108), integrated circuit, and/or combination of hardware and/or software as may serve a particular implementation. In some examples, controller 112 is configured to control light source 110 by turning light source 110 on and off and/or setting an intensity of light generated by light source 110. Controller 112 may be manually operated by a user, or may be programmed to control light source 110 automatically.

Light emitted by light source 110 may travel via an optical conduit 114 (e.g., a light pipe, a light guide, a waveguide, a single-mode optical fiber, and/or or a multi-mode optical fiber) to body 102 of a subject. In cases where optical conduit 114 is implemented by a light guide, the light guide may be spring loaded and/or have a cantilever mechanism to allow for conformably pressing the light guide firmly against body 102.

Body 102 may include any suitable turbid medium. For example, in some implementations, body 102 is a head or any other body part of a human or other animal. Alternatively, body 102 may be a non-living object. For illustrative purposes, it will be assumed in the examples provided herein that body 102 is a human head.

As indicated by arrow 120, the light emitted by light source 110 enters body 102 at a first location 122 on body 102. Accordingly, a distal end of optical conduit 114 may be positioned at (e.g., right above, in physical contact with, or physically attached to) first location 122 (e.g., to a scalp of the subject). In some examples, the light may emerge from optical conduit 114 and spread out to a certain spot size on body 102 to fall under a predetermined safety limit. At least a portion of the light indicated by arrow 120 may be scattered within body 102.

As used herein, "distal" means nearer, along the optical path of the light emitted by light source 110 or the light received by detector 104, to the target (e.g., within body 102) than to light source 110 or detector 104. Thus, the distal end of optical conduit 114 is nearer to body 102 than to light source 110, and the distal end of optical conduit 116 is nearer to body 102 than to detector 104. Additionally, as used herein, "proximal" means nearer, along the optical path of the light emitted by light source 110 or the light received by detector 104, to light source 110 or detector 104 than to body 102. Thus, the proximal end of optical conduit 114 is nearer to light source 110 than to body 102, and the proximal end of optical conduit 116 is nearer to detector 104 than to body 102.

As shown, the distal end of optical conduit 116 (e.g., a light pipe, a light guide, a waveguide, a single-mode optical fiber, and/or a multi-mode optical fiber) is positioned at (e.g., right above, in physical contact with, or physically attached to) output location 126 on body 102. In this manner, optical conduit 116 may collect at least a portion of the scattered light (indicated as light 124) as it exits body 102 at location 126 and carry light 124 to detector 104. Light 124 may pass through one or more lenses and/or other optical elements (not shown) that direct light 124 onto each of the photodetectors 106 included in detector 104.

Photodetectors 106 may be connected in parallel in detector 104. An output of each of photodetectors 106 may be accumulated to generate an accumulated output of detector 104. Processor 108 may receive the accumulated output and determine, based on the accumulated output, a temporal distribution of photons detected by photodetectors 106. Processor 108 may then generate, based on the temporal distribution, a histogram representing a light pulse response of a target (e.g., brain tissue, blood flow, etc.) in body 102. Example embodiments of accumulated outputs are described herein.

Figure 2:
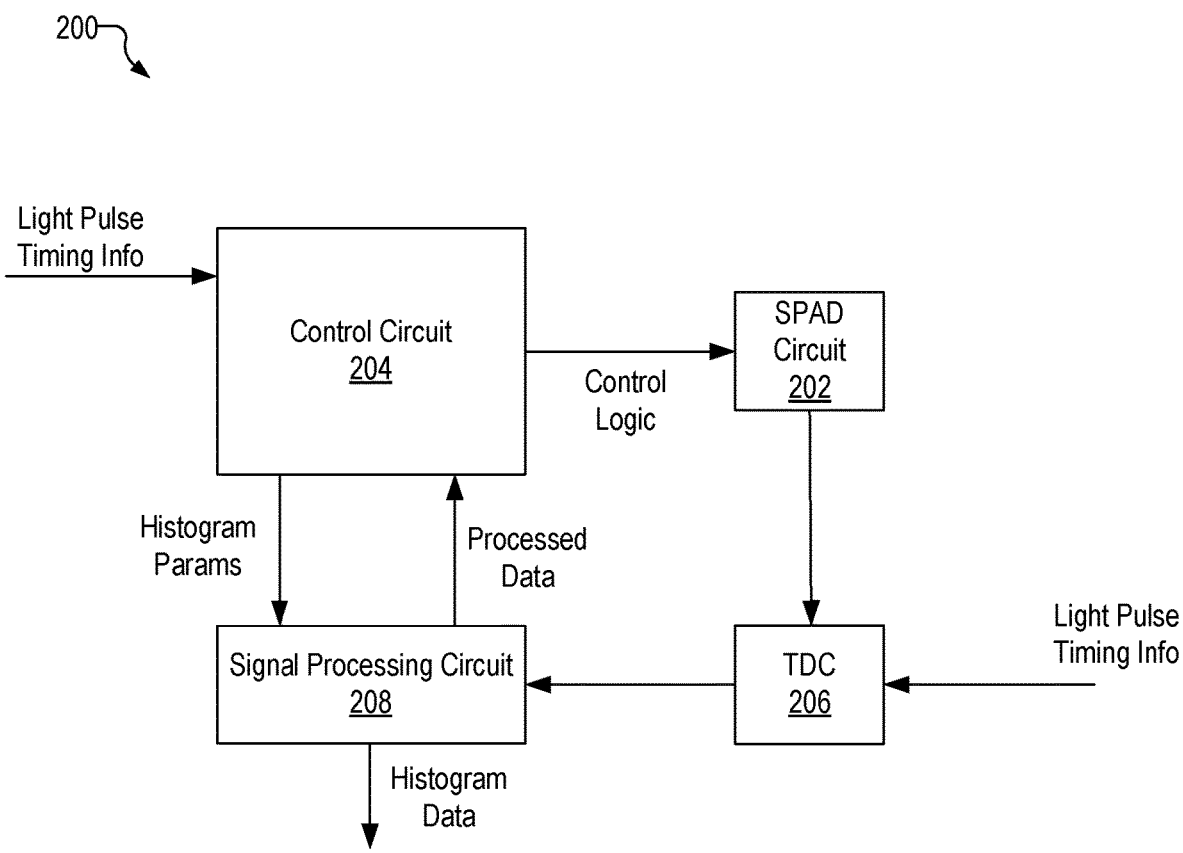
FIG. 2 illustrates an exemplary detector architecture.

FIG. 2 illustrates an exemplary detector architecture 200 that may be used in accordance with the systems and methods described herein. As shown, architecture 200 includes a SPAD circuit 202 that implements photodetector 106, a control circuit 204, a time-to-digital converter (TDC) 206, and a signal processing circuit 208. Architecture 200 may include additional or alternative components as may serve a particular implementation.

As mentioned, in some alternative examples, photodetector 106 may be configured to operate in a free-running mode such that photodetector 106 is not actively armed and disarmed (e.g., at the end of each predetermined gated time window represented by pulse wave 304). In contrast, while operating in the free-running mode, photodetector 106 may be configured to reset within a configurable time period after an occurrence of a photon detection event (i.e., after photodetector 106 detects a photon) and immediately begin detecting new photons. However, only photons detected within a desired time window (e.g., during each gated time window represented by pulse wave 304) may be included in the TPSF.

The fast gating circuit included in SPAD circuit 202 may be implemented in any suitable manner. For example, the fast gating circuit may be implemented by an active voltage source, a capacitor that is pre-charged with a bias voltage before a command is provided to arm the SPAD, and/or in any other suitable manner.

In some alternative configurations, SPAD circuit 202 does not include a fast gating circuit. In these configurations, the SPAD included in SPAD circuit 202 may be gated in any suitable manner or be configured to operate in a free running mode with passive quenching.

Control circuit 204 may be implemented by an application specific integrated circuit (ASIC) or any other suitable circuit configured to control an operation of various components within SPAD circuit 202. For example, control circuit 204 may output control logic that puts the SPAD included in SPAD circuit 202 in either an armed or a disarmed state.

In some examples, control circuit 204 may control an arming and a disarming of a SPAD included in SPAD circuit 202. Control circuit 204 may also control a programmable gate width, which specifies how long the SPAD is kept in an armed state before being disarmed.

Control circuit 204 is further configured to control signal processing circuit 208. For example, control circuit 204 may provide histogram parameters (e.g., time bins, number of light pulses, type of histogram, etc.) to signal processing circuit 208. Signal processing circuit 208 may generate histogram data in accordance with the histogram parameters. In some examples, control circuit 204 is at least partially implemented by controller 112.

TDC 206 is configured to measure a time difference between an occurrence of an output pulse generated by SPAD circuit 202 and an occurrence of a light pulse. To this end, TDC 206 may also receive the same light pulse timing information that control circuit 204 receives. TDC 206 may be implemented by any suitable circuitry as may serve a particular implementation.

Signal processing circuit 208 is configured to perform one or more signal processing operations on data output by TDC 206. For example, signal processing circuit 208 may generate histogram data based on the data output by TDC 206 and in accordance with histogram parameters provided by control circuit 204. To illustrate, signal processing circuit 208 may generate, store, transmit, compress, analyze, decode, and/or otherwise process histograms based on the data output by TDC 206. In some examples, signal processing circuit 208 may provide processed data to control circuit 204, which may use the processed data in any suitable manner. In some examples, signal processing circuit 208 is at least partially implemented by processor 108.

In some examples, each photodetector 106 (e.g., SPAD circuit 202) may have a dedicated TDC 206 associated therewith. For example, for an array of N photodetectors 106, there may be a corresponding array of N TDCs 206. Likewise, a single control circuit 204 and a single signal processing circuit 208 may be provided for a one or more photodetectors 106 and/or TDCs 206.

Figure 3:
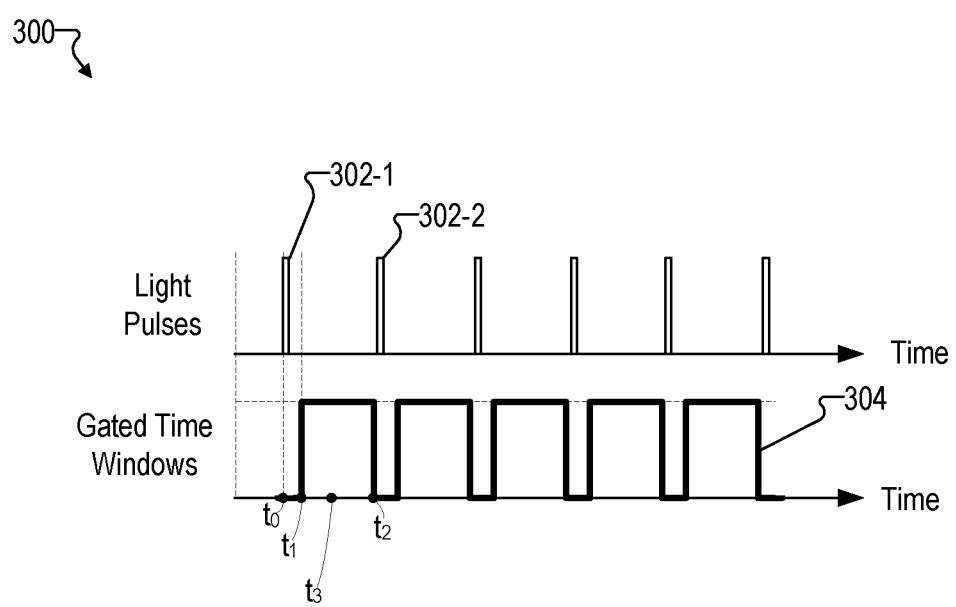
FIG. 3 illustrates an exemplary timing diagram for performing an optical measurement operation using an optical measurement system.

FIG. 3 illustrates an exemplary timing diagram 300 for performing an optical measurement operation using optical measurement system 100. Optical measurement system 100 may be configured to perform the optical measurement operation by directing light pulses (e.g., laser pulses) toward a target within a body (e.g., body 102). The light pulses may be short (e.g., 10-2000 picoseconds (ps)) and repeated at a high frequency (e.g., between 100,000 hertz (Hz) and 100 megahertz (MHz)). The light pulses may be scattered by the target and then detected by optical measurement system 100. Optical measurement system 100 may measure a time relative to the light pulse for each detected photon. By counting the number of photons detected at each time relative to each light pulse repeated over a plurality of light pulses, optical measurement system 100 may generate a histogram that represents a light pulse response of the target (e.g., a temporal point spread function (TPSF)). The terms histogram and TPSF are used interchangeably herein to refer to a light pulse response of a target.

For example, timing diagram 300 shows a sequence of light pulses 302 (e.g., light pulses 302-1 and 302-2) that may be applied to the target (e.g., tissue within a brain of a user, blood flow, a fluorescent material used as a probe in a body of a user, etc.). Timing diagram 300 also shows a pulse wave 304 representing predetermined gated time windows (also referred as gated time periods) during which photodetectors 106 are gated ON (i.e., armed) to detect photons. Referring to light pulse 302-1, light pulse 302-1 is applied at a time to. At a time $t_1$, a first instance of the predetermined gated time window begins. Photodetectors 106 may be armed at time $t_1$, enabling photodetectors 106 to detect photons scattered by the target during the predetermined gated time window. In this example, time $t_1$ is set to be at a certain time after time to, which may minimize photons detected directly from the laser pulse, before the laser pulse reaches the target. However, in some alternative examples, time $t_1$ is set to be equal to time to.

At a time $t_2$, the predetermined gated time window ends. In some examples, photodetectors 106 may be disarmed at time $t_2$. In other examples, photodetectors 106 may be reset (e.g., disarmed and re-armed) at time $t_2$ or at a time subsequent to time $t_2$. During the predetermined gated time window, photodetectors 106 may detect photons scattered by the target. Photodetectors 106 may be configured to remain armed during the predetermined gated time window such that photodetectors 106 maintain an output upon detecting a photon during the predetermined gated time window. For example, a photodetector 106 may detect a photon at a time $t_3$, which is during the predetermined gated time window between times $t_1$ and $t_2$. The photodetector 106 may be configured to provide an output indicating that the photodetector 106 has detected a photon. The photodetector 106 may be configured to continue providing the output until time $t_2$, when the photodetector may be disarmed and/or reset. Optical measurement system 100 may generate an accumulated output from the plurality of photodetectors. Optical measurement system 100 may sample the accumulated output to determine times at which photons are detected by photodetectors 106 to generate a TPSF.

As described herein, the systems, circuits, and methods described herein may obviate the need for the gated time windows described in connection with FIG. 3, thereby obviating the need for fast gating circuitry to be included in optical measurement system 100.

Figure 4:
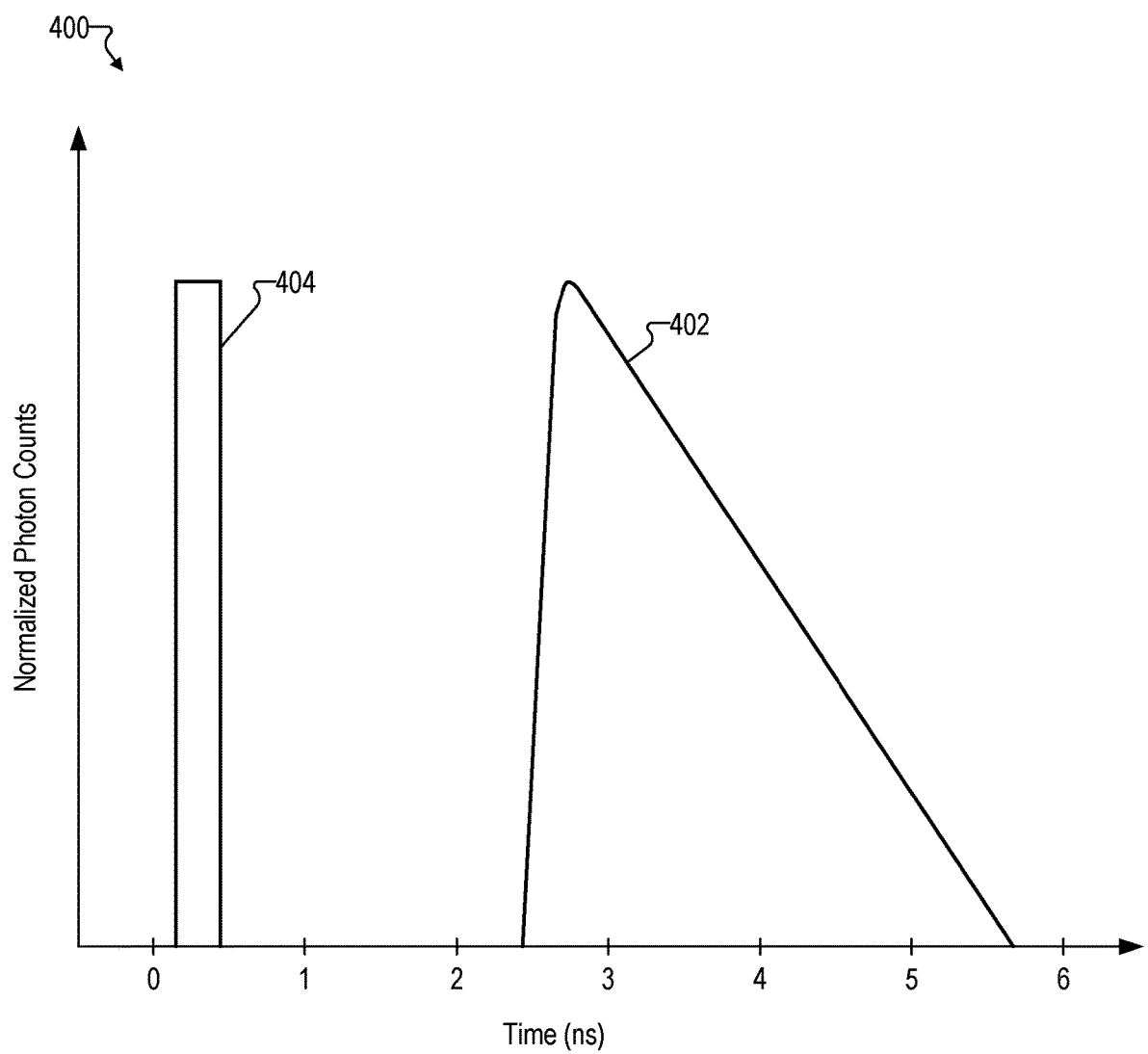
FIG. 4 illustrates a graph of an exemplary temporal point spread function that may be generated by an optical measurement system in response to a light pulse.

FIG. 4 illustrates a graph 400 of an exemplary TPSF 402 that may be generated by optical measurement system 100 in response to a light pulse 404 (which, in practice, represents a plurality of light pulses). Graph 400 shows a normalized count of photons on a y-axis and time bins on an x-axis. As shown, TPSF 402 is delayed with respect to a temporal occurrence of light pulse 404. In some examples, the number of photons detected in each time bin subsequent to each occurrence of light pulse 404 may be aggregated (e.g., integrated) to generate TPSF 402. TPSF 402 may be analyzed and/or processed in any suitable manner to determine or infer detected neural activity.

Optical measurement system 100 may be implemented by or included in any suitable device. For example, optical measurement system 100 may be included, in whole or in part, in a non-invasive wearable device (e.g., a headpiece) that a user may wear to perform one or more diagnostic, imaging, analytical, and/or consumer-related operations. The non-invasive wearable device may be placed on a user's head or other part of the user to detect neural activity. In some examples, such neural activity may be used to make behavioral and mental state analysis, awareness and predictions for the user.

Mental state described herein refers to the measured neural activity related to physiological brain states and/or mental brain states, e.g., joy, excitement, relaxation, surprise, fear, stress, anxiety, sadness, anger, disgust, contempt, contentment, calmness, focus, attention, approval, creativity, positive or negative reflections/attitude on experiences or the use of objects, etc. Further details on the methods and systems related to a predicted brain state, behavior, preferences, or attitude of the user, and the creation, training, and use of neuromes can be found in U.S. Provisional Patent Application No. 63/047,991, filed Jul. 3, 2020. Exemplary measurement systems and methods using biofeedback for awareness and modulation of mental state are described in more detail in U.S. patent application Ser. No. 16/364,338, filed Mar. 26, 2019, published as US2020/0196932A1. Exemplary measurement systems and methods used for detecting and modulating the mental state of a user using entertainment selections, e.g., music, film/video, are described in more detail in U.S. patent application Ser. No. 16/835,972, filed Mar. 31, 2020, published as US2020/0315510A1. Exemplary measurement systems and methods used for detecting and modulating the mental state of a user using product formulation from, e.g., beverages, food, selective food/drink ingredients, fragrances, and assessment based on product-elicited brain state measurements are described in more detail in U.S. patent application Ser. No. 16/853,614, filed Apr. 20, 2020, published as US2020/0337624A1. Exemplary measurement systems and methods used for detecting and modulating the mental state of a user through awareness of priming effects are described in more detail in U.S. patent application Ser. No. 16/885,596, filed May 28, 2020, published as US2020/0390358A1. These applications and corresponding U.S. publications are incorporated herein by reference in their entirety.

Figure 5:
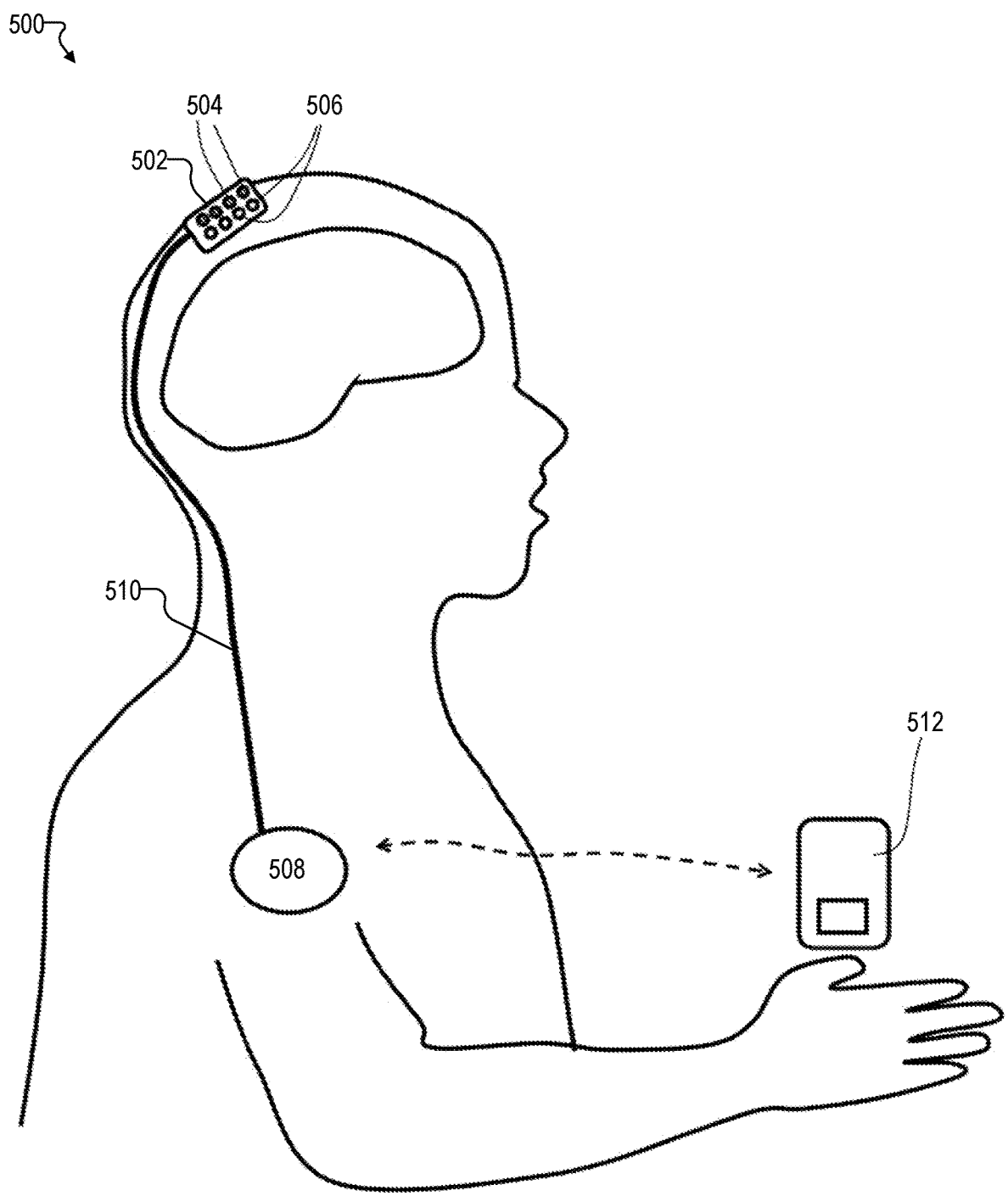
FIG. 5 shows an exemplary non-invasive wearable brain interface system.

FIG. 5 shows an exemplary non-invasive wearable brain interface system 500 ("brain interface system 500") that implements optical measurement system 100 (shown in FIG. 1). As shown, brain interface system 500 includes a head-mountable component 502 configured to be attached to a user's head. Head-mountable component 502 may be implemented by a cap shape that is worn on a head of a user. Alternative implementations of head-mountable component 502 include helmets, beanies, headbands, other hat shapes, or other forms conformable to be worn on a user's head, etc. Head-mountable component 502 may be made out of any suitable cloth, soft polymer, plastic, hard shell, and/or any other suitable material as may serve a particular implementation. Examples of headgears used with wearable brain interface systems are described more fully in U.S. Pat. No. 10,340,408, incorporated herein by reference in its entirety.

Head-mountable component 502 includes a plurality of detectors 504, which may implement or be similar to detector 104, and a plurality of light sources 506, which may be implemented by or be similar to light source 110. It will be recognized that in some alternative embodiments, head-mountable component 502 may include a single detector 504 and/or a single light source 506.

Brain interface system 500 may be used for controlling an optical path to the brain and for transforming photodetector measurements into an intensity value that represents an optical property of a target within the brain. Brain interface system 500 allows optical detection of deep anatomical locations beyond skin and bone (e.g., skull) by extracting data from photons originating from light source 506 and emitted to a target location within the user's brain, in contrast to conventional imaging systems and methods (e.g., optical coherence tomography (OCT)), which only image superficial tissue structures or through optically transparent structures.

Brain interface system 500 may further include a processor 508 configured to communicate with (e.g., control and/or receive signals from) detectors 504 and light sources 506 by way of a communication link 510. Communication link 510 may include any suitable wired and/or wireless communication link. Processor 508 may include any suitable housing and may be located on the user's scalp, neck, shoulders, chest, or arm, as may be desirable. In some variations, processor 508 may be integrated in the same assembly housing as detectors 504 and light sources 506.

As shown, brain interface system 500 may optionally include a remote processor 512 in communication with processor 508. For example, remote processor 512 may store measured data from detectors 504 and/or processor 508 from previous detection sessions and/or from multiple brain interface systems (not shown). Power for detectors 504, light sources 506, and/or processor 508 may be provided via a wearable battery (not shown). In some examples, processor 508 and the battery may be enclosed in a single housing, and wires carrying power signals from processor 508 and the battery may extend to detectors 504 and light sources 506. Alternatively, power may be provided wirelessly (e.g., by induction).

In some alternative embodiments, head mountable component 502 does not include individual light sources. Instead, a light source configured to generate the light that is detected by detector 504 may be included elsewhere in brain interface system 500. For example, a light source may be included in processor 508 and coupled to head mountable component 502 through optical connections.

Optical measurement system 100 may alternatively be included in a non-wearable device (e.g., a medical device and/or consumer device that is placed near the head or other body part of a user to perform one or more diagnostic, imaging, and/or consumer-related operations). Optical measurement system 100 may alternatively be included in a sub-assembly enclosure of a wearable invasive device (e.g., an implantable medical device for brain recording and imaging).

Figure 6:
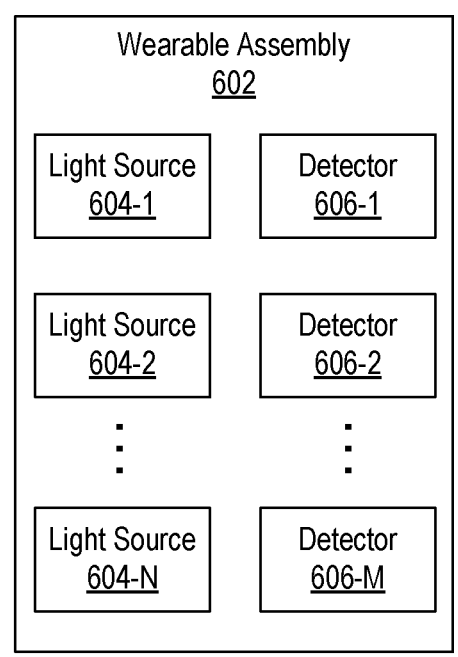
FIG. 6 shows an exemplary optical measurement system.

FIG. 6 shows an exemplary optical measurement system 600 in accordance with the principles described herein. Optical measurement system 600 may be an implementation of optical measurement system 100 and, as shown, includes a wearable assembly 602, which includes N light sources 604 (e.g., light sources 604-1 through 604-N) and M detectors 606 (e.g., detectors 606-1 through 606-M). Optical measurement system 600 may include any of the other components of optical measurement system 100 as may serve a particular implementation. N and M may each be any suitable value (i.e., there may be any number of light sources 604 and detectors 606 included in optical measurement system 600 as may serve a particular implementation).

Light sources 604 are each configured to emit light (e.g., a sequence of light pulses) and may be implemented by any of the light sources described herein. Detectors 606 may each be configured to detect arrival times for photons of the light emitted by one or more light sources 604 after the light is scattered by the target. For example, a detector 606 may include a photodetector configured to generate a photodetector output pulse in response to detecting a photon of the light and a TDC configured to record a timestamp symbol in response to an occurrence of the photodetector output pulse, the timestamp symbol representative of an arrival time for the photon (i.e., when the photon is detected by the photodetector).

Wearable assembly 602 may be implemented by any of the wearable devices, modular assemblies, and/or wearable units described herein. For example, wearable assembly 602 may be implemented by a wearable device (e.g., headgear) configured to be worn on a user's head. Wearable assembly 602 may additionally or alternatively be configured to be worn on any other part of a user's body.

Optical measurement system 600 may be modular in that one or more components of optical measurement system 600 may be removed, changed out, or otherwise modified as may serve a particular implementation. Additionally or alternatively, optical measurement system 100 may be modular such that one or more components of optical measurement system 100 may be housed in a separate housing (e.g., module) and/or may be movable relative to other components. Exemplary modular multimodal measurement systems are described in more detail in U.S. patent application Ser. No. 17/176,460, filed Feb. 16, 2021, U.S. patent application Ser. No. 17/176,470, filed Feb. 16, 2021, U.S. patent application Ser. No. 17/176,487, filed Feb. 16, 2021, U.S. Provisional Patent Application No. 63/038,481, filed Jun. 12, 2020, and U.S. patent application Ser. No. 17/176,560, filed Feb. 16, 2021, which applications are incorporated herein by reference in their respective entireties.

Figure 7:
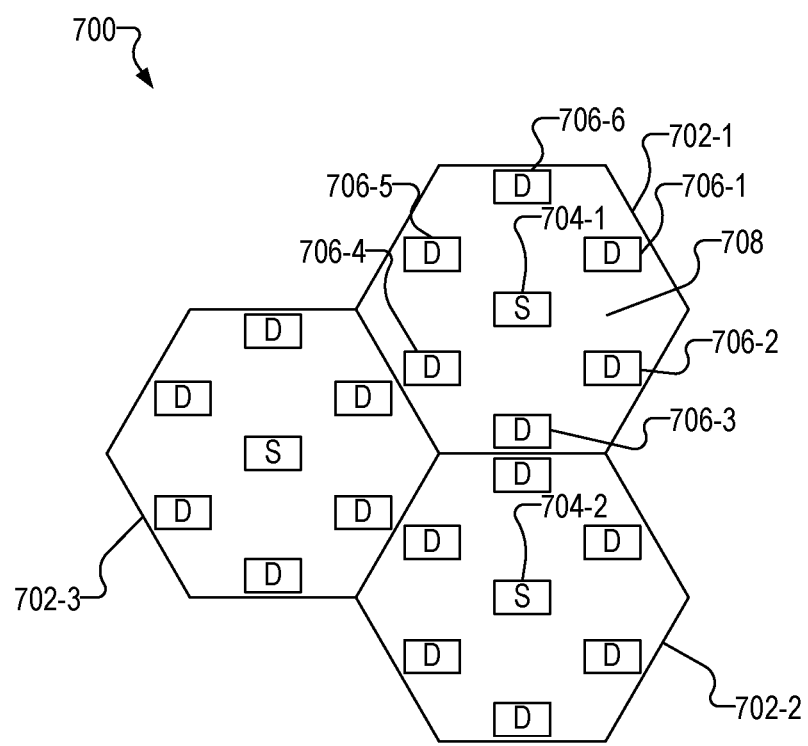
FIG. 7 shows an illustrative modular assembly.

FIG. 7 shows an illustrative modular assembly 700 that may implement optical measurement system 600. Modular assembly 700 is illustrative of the many different implementations of optical measurement system 600 that may be realized in accordance with the principles described herein.

As shown, modular assembly 700 includes a plurality of modules 702 (e.g., modules 702-1 through 702-3). While three modules 702 are shown to be included in modular assembly 700, in alternative configurations, any number of modules 702 (e.g., a single module up to sixteen or more modules) may be included in modular assembly 700.

Each module 702 includes a light source (e.g., light source 704-1 of module 702-1 and light source 704-2 of module 702-2) and a plurality of detectors (e.g., detectors 706-1 through 706-6 of module 702-1). In the particular implementation shown in FIG. 7, each module 702 includes a single light source and six detectors. Each light source is labeled "S" and each detector is labeled "D".

Each light source depicted in FIG. 7 may be implemented by one or more light sources similar to light source 110 and may be configured to emit light directed at a target (e.g., the brain).

Each light source depicted in FIG. 7 may be located at a center region of a surface of the light source's corresponding module. For example, light source 704-1 is located at a center region of a surface 708 of module 702-1. In alternative implementations, a light source of a module may be located away from a center region of the module.

Each detector depicted in FIG. 7 may implement or be similar to detector 104 and may include a plurality of photodetectors (e.g., SPADs) as well as other circuitry (e.g., TDCs), and may be configured to detect arrival times for photons of the light emitted by one or more light sources after the light is scattered by the target.

The detectors of a module may be distributed around the light source of the module. For example, detectors 706 of module 702-1 are distributed around light source 704-1 on surface 708 of module 702-1. In this configuration, detectors 706 may be configured to detect photon arrival times for photons included in light pulses emitted by light source 704-1. In some examples, one or more detectors 706 may be close enough to other light sources to detect photon arrival times for photons included in light pulses emitted by the other light sources. For example, because detector 706-3 is adjacent to module 702-2, detector 706-3 may be configured to detect photon arrival times for photons included in light pulses emitted by light source 704-2 (in addition to detecting photon arrival times for photons included in light pulses emitted by light source 704-1).

In some examples, the detectors of a module may all be equidistant from the light source of the same module. In other words, the spacing between a light source (i.e., a distal end portion of a light source optical conduit) and the detectors (i.e., distal end portions of optical conduits for each detector) are maintained at the same fixed distance on each module to ensure homogeneous coverage over specific areas and to facilitate processing of the detected signals. The fixed spacing also provides consistent spatial (lateral and depth) resolution across the target area of interest, e.g., brain tissue. Moreover, maintaining a known distance between the light source, e.g., light emitter, and the detector allows subsequent processing of the detected signals to infer spatial (e.g., depth localization, inverse modeling) information about the detected signals. Detectors of a module may be alternatively disposed on the module as may serve a particular implementation.

Figure 8A:
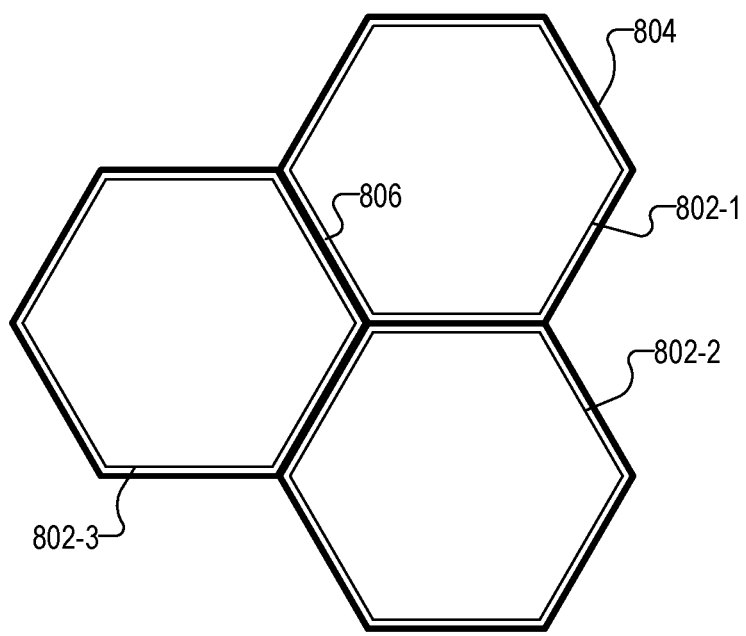
FIGS. 8A-8B show an exemplary implementation of the modular assembly of FIG. 7.
Figure 8B:
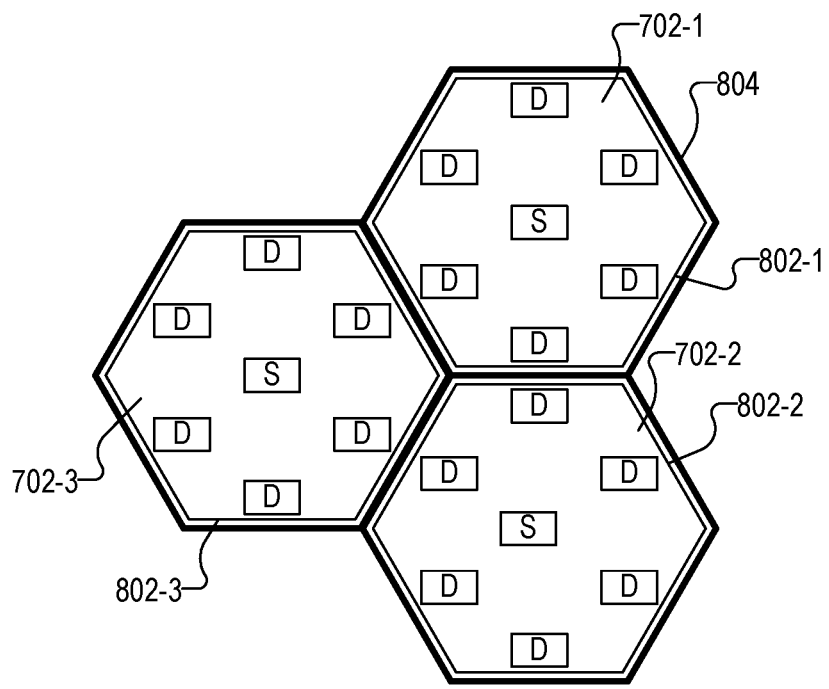

In FIG. 7, modules 702 are shown to be adjacent to and touching one another. Modules 702 may alternatively be spaced apart from one another. For example, FIGS. 8A-8B show an exemplary implementation of modular assembly 700 in which modules 702 are configured to be inserted into individual slots 802 (e.g., slots 802-1 through 802-3, also referred to as cutouts) of a wearable assembly 804. In particular, FIG. 8A shows the individual slots 802 of the wearable assembly 804 before modules 702 have been inserted into respective slots 802, and FIG. 8B shows wearable assembly 804 with individual modules 702 inserted into respective individual slots 802.

Wearable assembly 804 may implement wearable assembly 602 and may be configured as headgear and/or any other type of device configured to be worn by a user.

As shown in FIG. 8A, each slot 802 is surrounded by a wall (e.g., wall 806) such that when modules 702 are inserted into their respective individual slots 802, the walls physically separate modules 702 one from another. In alternative embodiments, a module (e.g., module 702-1) may be in at least partial physical contact with a neighboring module (e.g., module 702-2).

Each of the modules described herein may be inserted into appropriately shaped slots or cutouts of a wearable assembly, as described in connection with FIGS. 8A-8B. However, for ease of explanation, such wearable assemblies are not shown in the figures.

As shown in FIGS. 7 and 8B, modules 702 may have a hexagonal shape. Modules 702 may alternatively have any other suitable geometry (e.g., in the shape of a pentagon, octagon, square, rectangular, circular, triangular, free-form, etc.).

Figure 9A:
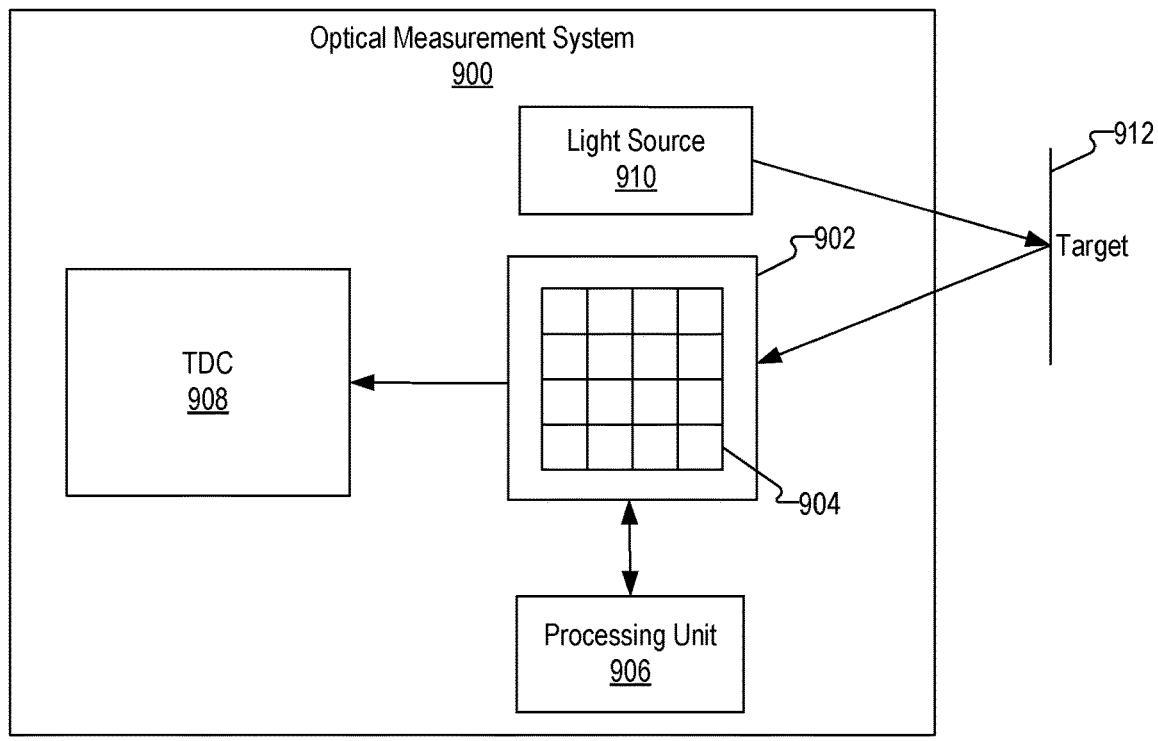
FIGS. 9A-9B show exemplary optical measurement systems.

FIG. 9A shows an exemplary optical measurement system 900, which may be an implementation or a portion of optical measurement system 100. Optical measurement system 900 includes a detector 902 (e.g., an implementation of detector 104) that includes an array of photodetectors 904 (e.g., implementations of photodetector 106). Optical measurement system 900 further includes a processing unit 906 (e.g., an implementation and/or portion of processor 108, processor 508, etc.) and a TDC 908 (e.g., an implementation of TDC 206). Optical measurement system 900 further includes a light source 910 (e.g., an implementation of light source 110) configured to emit light directed at a target 912.

Photodetectors 904 may be configured to detect photons of the light emitted by light source 910 after the light is scattered by target 912. Photodetectors 904 may each output a signal based on detecting a photon of the light. The signal may be output to TDC 908 (which in some examples may be implemented as an array of TDCs), which may be configured to record a time based on the detecting of the photons by photodetectors 904. Optical measurement system 900 may generate a histogram based on the times recorded by TDC 908, which may represent a temporal distribution of photons detected by photodetectors 904.

However, due to device impurities and/or defects, each of photodetectors 904 may exhibit some level of noise. One example measurement of such noise is a dark count rate (DCR), which may be measured by counting output signals generated by photodetector 904 despite photodetector 904 not detecting a photon. For instance, optical measurement system 900 may use a time period during which light source 910 is not emitting light and count for each photodetector 904 how many output signals are generated by photodetector 904 during the time period (despite an absence of photons to be detected by photodetector 904). As each output signal generated by photodetector 904 indicates a detecting of a photon, if such a signal is produced while light source 910 is not emitting light, the signals may be considered noise, rather than a reliable output. A count of such output signals may be a dark count for photodetector 904. The dark count divided by a time period (e.g., per second, per minute, per millisecond, etc.) may define a DCR for photodetector 904.

Further, due to process variation, the DCR may vary among photodetectors 904 of detector 902. By removing output from relatively noisy photodetectors 904 from histograms generated based on output of detector 902, optical measurement system 900 may generate more accurate histograms and/or provide more sensitive measurements of scattered light than histograms generated based on outputs of all photodetectors 904.

Thus, optical measurement system 900 may determine a noise level (e.g., a DCR) for each photodetector 904. The noise level may be compared to a predetermined threshold. If the noise level meets (e.g., by being equal to or greater than) the threshold noise level, the output of the corresponding photodetector 904 may be prevented from being used in generating the histogram based on the temporal distribution of photons detected by detector 902.

The DCR for each photodetector 904 may be determined in any suitable manner. For instance, optical measurement system 900 may generate a histogram for each photodetector 904, e.g., based on a plurality of time periods while light source 910 is not emitting light, with each photodetector 904 outputting signals to TDC 908 to determine dark counts for each photodetector 904.

Figure 9B:
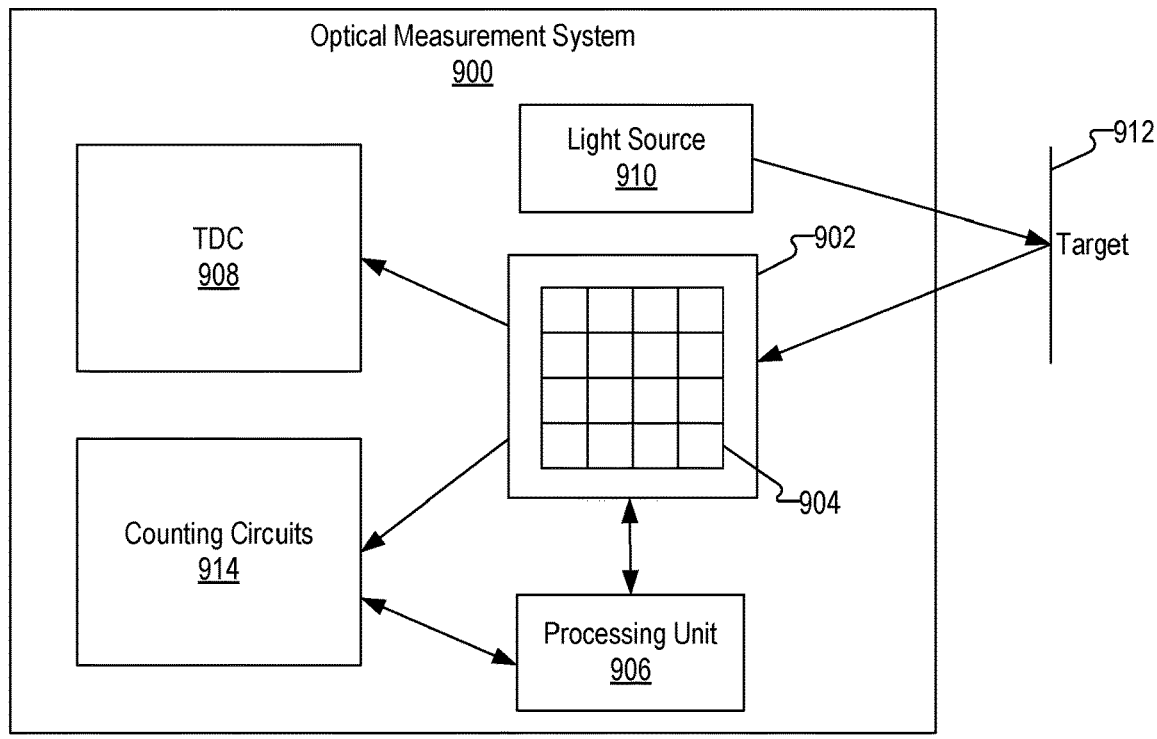

Additionally or alternatively, optical measurement system 900 may include a plurality of counting circuits. FIG. 9B illustrates optical measurement system 900 including a plurality of counting circuits 914. The plurality of counting circuits 914 may include a respective counting circuit 914 for each photodetector 904. As shown, counting circuits 914 may be implemented as an array of counting circuits 914 coupled to photodetectors 904. Alternatively or additionally, counting circuits 914 may be included in detector 902. Each counting circuit 914 may be implemented by any suitable combination of hardware and/or software.

Optical measurement system 900 (e.g., processing unit 906) may direct counting circuits 914 to count output signals from each respective photodetector 904 concurrently during one or more time periods while light source 910 is not emitting light. In this manner, optical measurement system 900 may determine the DCRs for all photodetectors 904 at once. Optical measurement system 900 may thus periodically measure DCRs of photodetectors 904, such as on startup or any other suitable period (e.g., manufacturing, calibration, and/or any other testing period).

Processing unit 906 may compare the measured DCRs of photodetectors 904 to a predetermined threshold noise level. The predetermined threshold may be any suitable noise level, which, for example, may depend on a desired sensitivity level of optical measurement system 900. In some examples, the predetermined threshold level may be adjustable (e.g., for different applications of optical measurement system 900). For photodetectors 904 for which the DCR meets (e.g., is above, equal to or greater than, etc.) the predetermined threshold, processing unit 906 may prevent an output of such photodetectors 904 from being used in generating the histogram.

Figure 10A:
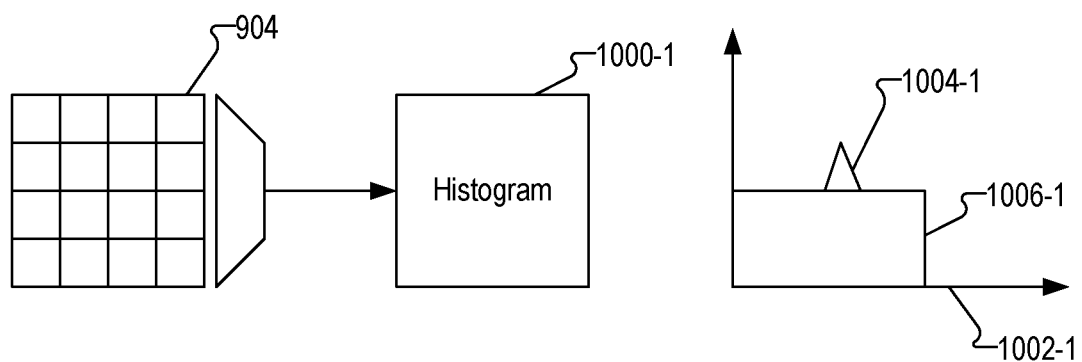
FIGS. 10A-10B illustrate exemplary histograms.
Figure 10B:
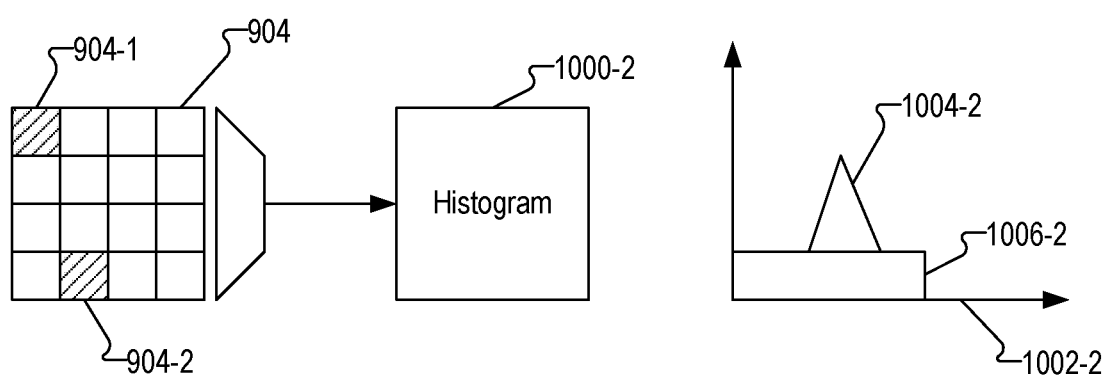

For example, FIGS. 10A and 10B illustrate exemplary histograms 1000 (e.g., histogram 1000-1 and histogram 1000-2) that may be generated by optical measurement system 900. FIG. 10A shows outputs of photodetectors 904 combined to generate histogram 1000-1 that depicts a temporal distribution of photons detected by photodetectors 904. A graph 1002-1 shows histogram 1000-1, which illustrates an intensity of a signal 1004-1 of histogram 1000-1 compared to a noise level 1006-1 of histogram 1000-1. As histogram 1000-1 is generated based on outputs of all photodetectors 904, noise level 1006-1 may be relatively high, which may obscure some of signal 1004-1. The relatively high noise level 1006-1 may result in a higher signal-to-noise ratio (SNR) and consequently less useful information extracted from histogram 1000-1.

In contrast, FIG. 10B shows two of photodetectors 904, a photodetector 904-1 and a photodetector 904-2 that have been disabled, e.g., by processing unit 906. Processing unit 906 may measure noise levels for photodetectors 904 and determine that noise levels for photodetector 904-1 and photodetector 904-2 meet a predetermined threshold. Based on the determination, processing unit 906 may disable photodetector 904-1 and photodetector 904-2 to prevent outputs of photodetector 904-1 and photodetector 904-2 from being included in generating histogram 1000-2.

A graph 1002-2 shows histogram 1000-2, which illustrates an intensity of a signal 1004-2 of histogram 1000-2 compared to a noise level 1006-2 of histogram 1000-2. As histogram 1000-2 is generated based on outputs of photodetectors 904 not including noisy photodetectors (e.g., photodetector 904-1 and photodetector 904-2), noise level 1006-2 may be lower than noise level 1006-1. While the intensity of signal 1004-2 may also be lower than the intensity of signal 1004-1, an SNR of histogram 1000-2 may be higher than the SNR of histogram 1000-1 as the output of the noisy photodetectors are not included in histogram 1000-2. In some examples, the intensity of signal 1004-2 may be the same as the intensity of signal 1004-1, which may result in an even higher SNR. The higher SNR of histogram 1000-2 may allow optical measurement system 900 to extract more information from histogram 1000-2 that is based on outputs of photodetectors 904 not including photodetectors 904-1 and 904-2 that have a noise level that meets the predetermined threshold.

Histogram 1000-2 may be normalized, for example, based on a number of photodetectors 904 that are included (or excluded) in generating histogram 1000-2. Additionally or alternatively, histogram 1000-2 may be normalized based on a peak of histogram 1000-2. Normalizing histogram 1000-2 may allow optical measurement system 900 to compare histograms generated by various detectors of optical measurement system 900 that may have different numbers of photodetectors disabled or otherwise prevented from being included in generating a respective histogram. Such normalizing may be performed by detector 902 and/or by processing unit 906.

In some examples, optical measurement system 900 may correct histograms based on noise levels of photodetectors 904. For instance, the DCR measured for each of photodetectors 904 may allow optical measurement system 900 to subtract the DCR from histograms generated based on photodetectors 904 or otherwise correct for measured noise levels using any suitable algorithm. Additionally or alternatively, the measured noise level may be included with the histogram as metadata to provide additional information.

Figure 11:
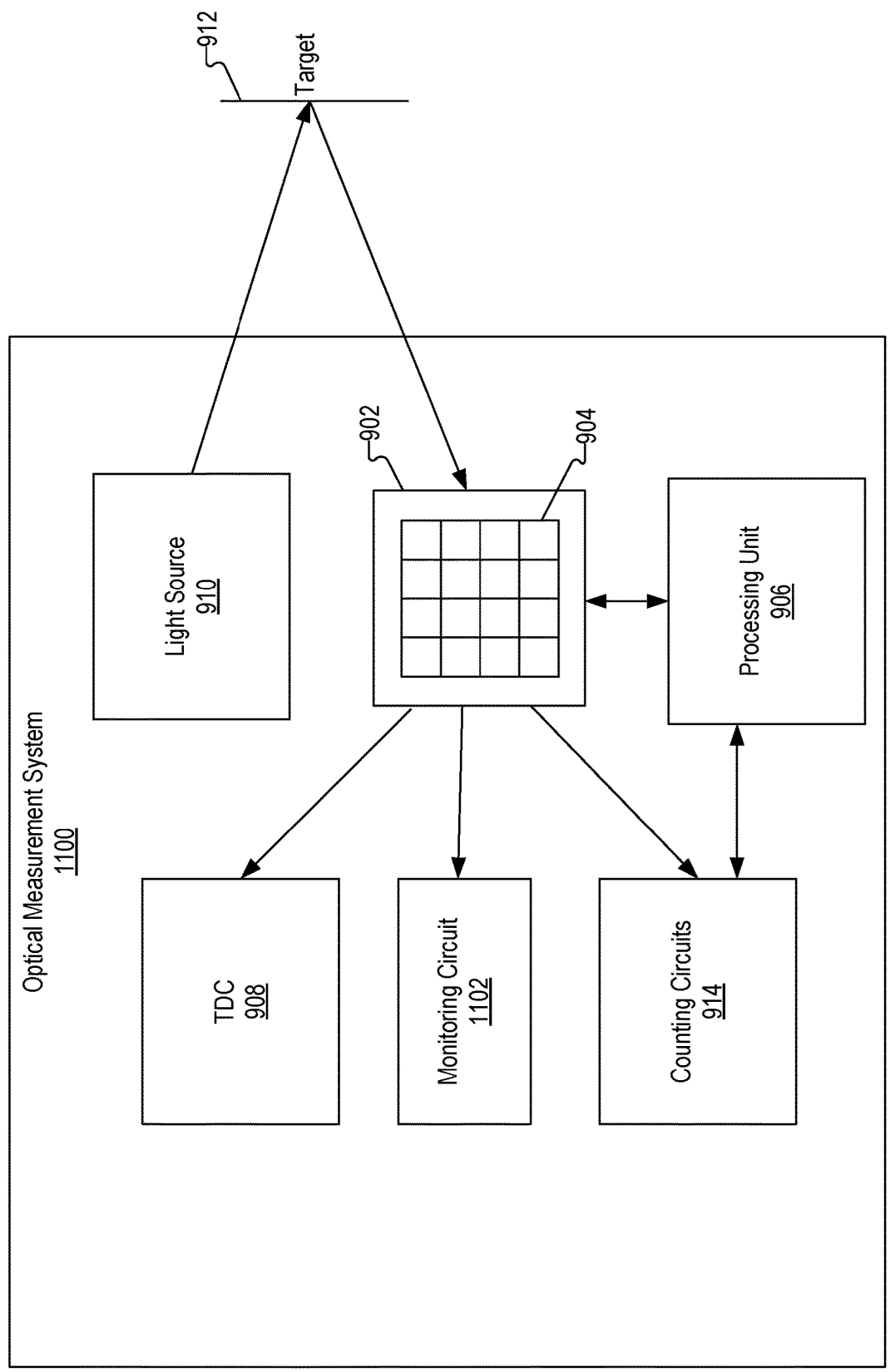
FIG. 11 shows an exemplary optical measurement system.

FIG. 11 shows another exemplary optical measurement system 1100, which may be an implementation or a portion of optical measurement system 100. Optical measurement system 1100 may be similar to optical measurement system 900, including detector 902 that includes photodetectors 904, processing unit 906, TDC 908, and light source 910. Optical measurement system 1100 may further include a monitoring circuit 1102. Similar to optical measurement system 900, optical measurement system 1100 (e.g., processing unit 906) may be configured to prevent outputs of photodetectors 904 that are determined to have a noise level that meets a predetermined threshold from being used in generating histograms.

Processing unit 906 may prevent the outputs of noisy photodetectors 904 from being used in generating histograms in any suitable manner. For instance, processing unit 906 may disable photodetectors 904 that are determined to have noise levels that meet the predetermined threshold. Additionally or alternatively, processing unit may switch the output of noisy photodetectors 904 from being directed to TDC 908 to instead being directed to monitoring circuit 1102.

Monitoring circuit 1102 may be configured to monitor, based on outputs of noisy photodetectors 904, any suitable characteristics of optical measurement system 1100. For example, a DCR of photodetectors 904 may vary based on temperature. Therefore, based on a change in the DCR of noisy photodetectors 904, monitoring circuit 1102 may determine a temperature associated with optical measurement system 1100 and/or a change in temperature associated with optical measurement system 1100.

Additionally or alternatively, monitoring circuit 1102 may be configured to determine a peak location of a light pulse emitted by light source 910. For instance, the peak location of the light pulse may be used as a reference point to determine measurement windows of interest, which may be correlated to locations of interest within target 912. While noisy photodetectors 904 that output signals to monitoring circuit 1102 may have a relatively high noise level (e.g., a relatively low SNR), such noisy photodetectors 904 may still provide reliable output signals for outputs of light source 910 that have a relatively high intensity, such as a peak of a light pulse. Thus, monitoring circuit 1102 may use the outputs of noisy photodetectors 904 to determine and/or track the peak location of light pulses emitted by light source 910.

Additionally or alternatively, monitoring circuit 1102 may be configured to determine an excess bias voltage of photodetectors 904. For instance, a breakdown voltage of photodetectors 904 may vary based on temperature. As temperature rises, the breakdown voltage of photodetectors 904 may rise, while a bias voltage of photodetectors 904 may remain constant. A difference between the bias voltage and the breakdown voltage may be the excess bias voltage of photodetectors 904, which may affect a sensitivity of photodetectors 904. Thus, monitoring circuit 1102 may include one or more components configured to measure the excess bias voltage of noisy photodetectors 904 to monitor the sensitivity of photodetectors 904.

In some examples, monitoring circuit 1102 may provide an output (e.g., to processing unit 906) so that optical measurement system 1100 may adjust parameters based on the output of monitoring circuit 1102. For example, optical measurement system 1100 may adjust. based on the output of monitoring circuit 1102, a measurement window of photodetectors 904, an excess bias voltage level of photodetectors 904, a temperature associated with optical measurement system 1100, and/or any other suitable parameters of optical measurement system 1100.

While DCR has been used as one example noise level of photodetectors 904, optical measurement system 1100 may use any suitable noise level measurement to determine whether to prevent an output of a photodetector from being used to generate a histogram. For instance, processing unit 906 may measure an SNR of photodetectors 904 in addition to or instead of DCR. Processing unit 906 may measure an SNR of photodetectors 904 in any suitable manner. For example, processing unit 906 may direct counting circuits 914 for photodetectors 904 to measure a dark count as described herein. Processing unit 906 may also direct counting circuits 914 to count signals during another one or more periods of time while light source 910 is emitting light (e.g., a light with known characteristics such as a uniform light) to determine a light count. The light count divided by the dark count for each photodetector 904 may define an SNR for each photodetector 904. For noise level measurements such as SNR where a lower value indicates a higher noise level, processing unit 906 may determine that the noise level of photodetector 904 meets the predetermined threshold when the measured SNR (or other such noise level measurement) is below (or less than or equal to, etc.) the predetermined threshold.

In some examples, the noise level measured by processing unit 906 may be both an SNR and a DCR. For instance, processing unit 906 may compare the DCR measured for each photodetector 904 to a predetermined DCR threshold. Processing unit 906 may prevent photodetectors 904 that have a DCR above the predetermined DCR threshold from being used in generating histograms. In addition, processing unit 906 may compare the SNR measured for each photodetector 904 to a predetermined SNR threshold. Processing unit 906 may prevent photodetectors 904 that have an SNR below the predetermined SNR threshold from being used in generating histograms. While photodetectors 904 that have a DCR below the predetermined DCR threshold may be relatively less noisy, some such photodetectors 904 may also not contribute much signal to the generated histogram.

Thus, while one noise level measurement (DCR) of such photodetectors 904 may be relatively low, the signal level may also be low, resulting in a high SNR. Such instances may occur, for example, when some photodetectors 904 do not receive many photons due to how light scatters off of target 912. Similar determinations may be made using a light count rate instead of or in addition to the SNR (e.g., a light count rate that is below a predetermined threshold light count rate may result in an SNR that meets the predetermined SNR threshold regardless of a corresponding DCR). Thus, in these examples, processing unit 906 may determine that a noise level of a photodetector 904 meets the predetermined threshold when a DCR of photodetector 904 is higher than the predetermined DCR threshold and/or an SNR (and/or light count) of photodetector 904 is lower than the predetermined SNR (and/or light count) threshold.

Figure 12A:
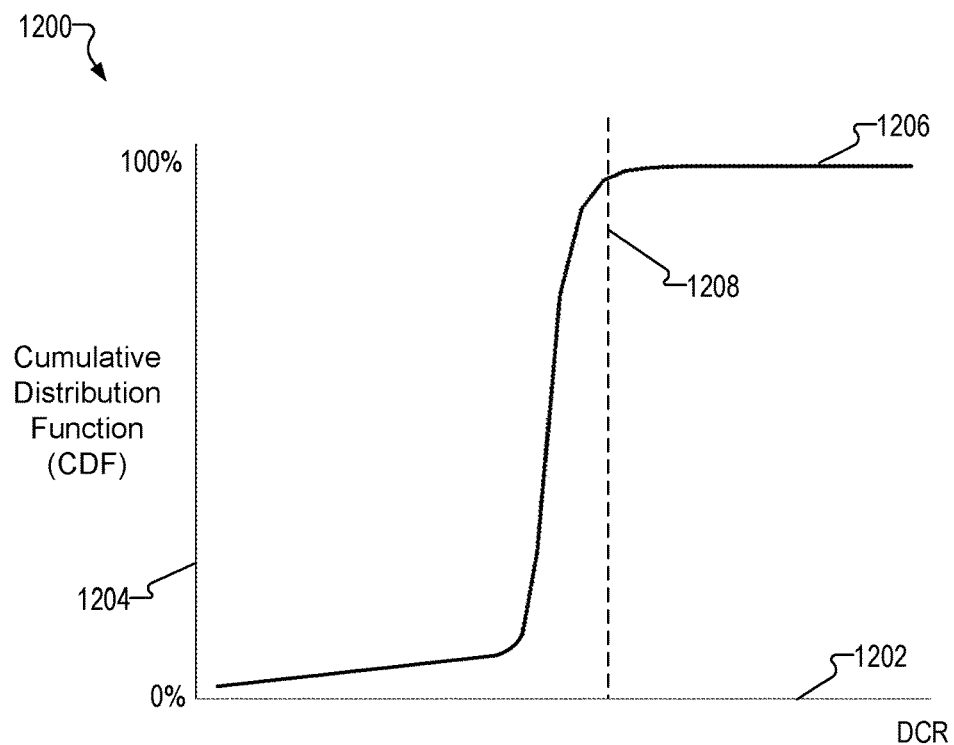
FIGS. 12A-12B illustrate exemplary noise thresholds.
Figure 12B:
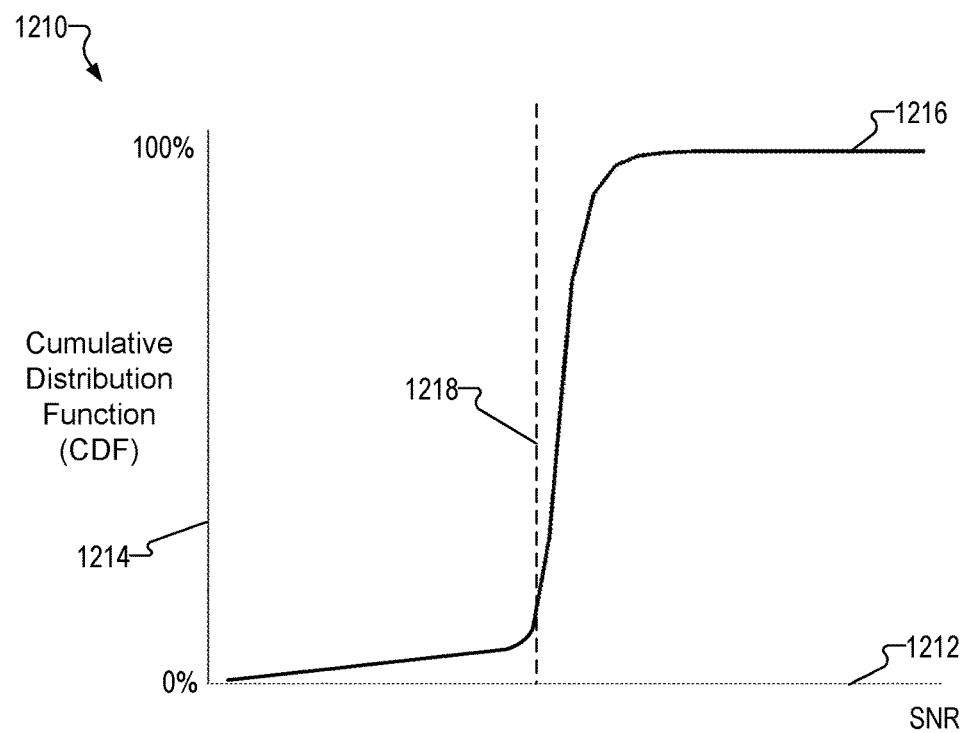

While the predetermined noise level thresholds may include specific values (e.g., an SNR of 0.1, a DCR of 100/sec, etc.), the predetermined noise level thresholds may also include relative values, such as based on a distribution of noise levels of photodetectors 904. For instance, FIGS. 12A and 12B illustrate exemplary predetermined noise level thresholds based on distributions of noise levels of photodetectors 904. FIG. 12A shows a graph 1200 that includes an x-axis 1202 representing DCR and a y-axis 1204 representing a cumulative distribution function (CDF) of photodetectors 904. A line 1206 shows a CDF of photodetectors 904 plotted against the DCR. Line 1206 shows that a majority of photodetectors 904 are distributed in a specific range of DCR levels, as shown by a steep rise in line 1206. A dotted line 1208 may represent an example predetermined DCR threshold based on the distribution. This predetermined DCR threshold may be set in any suitable manner. For example, as shown, the predetermined DCR threshold may be set to a value after the steep rise in line 1206. Photodetectors 904 that have a DCR above the predetermined DCR threshold may be considered as meeting the predetermined noise level threshold. In this manner, the relatively noisy photodetectors 904 may be disabled or otherwise prevented from being included in generating histograms.

FIG. 12B shows a graph 1210 that illustrates a similar predetermined noise level threshold based on SNR. Graph 1210 includes an x-axis 1212 representing SNR and a y-axis 1214 representing a CDF of photodetectors 904. A line 1216 shows a CDF of photodetectors 904 plotted against the SNR. Line 1216 shows that a majority of photodetectors 904 are distributed in a specific range of SNR levels as shown by a steep rise in line 1216. A dotted line 1218 may represent an example predetermined SNR threshold based on the distribution. This predetermined SNR threshold may be set in any suitable manner. For example, as shown, the predetermined SNR threshold may be set to a value before the steep rise in line 1216. As described, for SNR, photodetectors 904 that have an SNR value below the predetermined SNR threshold may be considered as meeting the predetermined noise level threshold.

Figure 13:
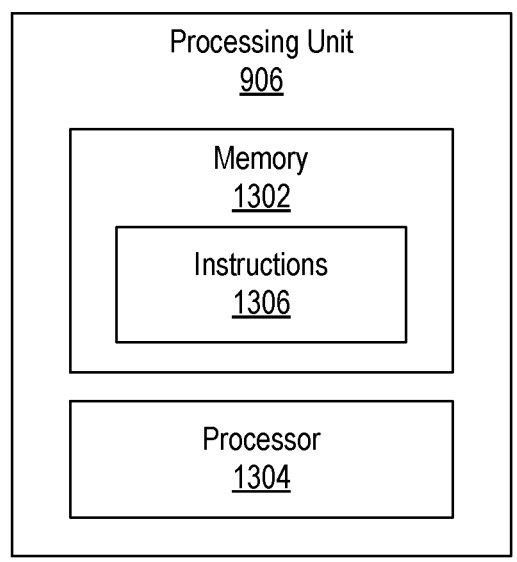
FIG. 13 illustrates an exemplary implementation of a processing unit.

FIG. 13 illustrates an exemplary implementation of processing unit 906 in which processing unit 906 includes a memory 1302 and a processor 1304 configured to be selectively and communicatively coupled to one another. In some examples, memory 1302 and processor 1304 may be distributed between multiple devices and/or multiple locations as may serve a particular implementation.

Memory 1302 may be implemented by any suitable non-transitory computer-readable medium and/or non-transitory processor-readable medium, such as any combination of non-volatile storage media and/or volatile storage media. Exemplary non-volatile storage media include, but are not limited to, read-only memory, flash memory, a solid-state drive, a magnetic storage device (e.g., a hard drive), ferroelectric random-access memory ("RAM"), and an optical disc. Exemplary volatile storage media include, but are not limited to, RAM (e.g., dynamic RAM).

Memory 1302 may maintain (e.g., store) executable data used by processor 1304 to perform one or more of the operations described herein. For example, memory 1302 may store instructions 1306 that may be executed by processor 1304 to perform any of the operations described herein. Instructions 1306 may be implemented by any suitable application, program (e.g., sound processing program), software, code, and/or other executable data instance. Memory 1302 may also maintain any data received, generated, managed, used, and/or transmitted by processor 1304.

For example, memory 1302 may store data representative of photodetectors 904 (e.g., a unique address identifier for each photodetector 904). Memory 1302 may also store data indicating which of photodetectors 904 have a noise level that meets the predetermined threshold. Processing unit 906 may periodically measure the noise levels of photodetectors 904 to determine which outputs of photodetectors 904 to prevent from being used in generating histograms. Processing unit 906 (e.g., processor 1304) may use the data stored in memory 1302 so that processing unit 906 skips over measuring the noise levels of those already indicated as having a noise level that meets the predetermined threshold. Thus, processing unit 906 may periodically measure the noise levels of photodetectors 904 that are not represented in memory 1302 as having noise levels that meet the predetermined threshold.

As one example, memory 1302 may be implemented by a one-time programmable (OTP) memory. The OTP memory may include a bit corresponding to each of photodetectors 904. Processing unit 906 may record in the OTP memory by programming (e.g., fusing) the bit for each photodetector 904 that processing unit 906 determines has a noise level that meets the predetermined threshold. In subsequent checks, processing unit 906 may skip over the photodetectors 904 corresponding to programmed bits and measure noise levels for photodetectors 904 corresponding to unprogrammed bits.

Processor 1304 may be configured to perform (e.g., execute instructions 1306 stored in memory 1302 to perform) various operations described herein. For example, processor 1304 may be configured to perform any of the operations described herein as being performed by processing unit 906.

In some examples, processing unit 906 may be included in the same wearable assembly (e.g., wearable assembly 602) that include light source 910, photodetectors 904, and/or TDC 908. Alternatively, processing unit 906 is not included in the same wearable assembly (e.g., wearable assembly 602) that include light source 910, photodetectors 904, and/or TDC 908.

To illustrate, processing unit 906 may be included in a wearable device separate from wearable assembly 602. For example, processing unit 906 may be included in a wearable device configured to be worn off the head while wearable assembly 602 is worn on the head. In these examples, one or more communication interfaces (e.g., cables, wireless interfaces, etc.) may be used to facilitate wearable assembly 602 and the separate wearable device.

Additionally or alternatively, processing unit 906 may be remote from the user (i.e., not worn by the user). For example, processing unit 906 may be implemented by a stand-alone computing device communicatively coupled to wearable assembly 602 by way of one or more communication interfaces (e.g., cables, wireless interfaces, etc.).

FIGS. 14-18 illustrate embodiments of a wearable device 1400 that includes elements of the optical detection systems described herein. In particular, the wearable devices 1400 shown in FIGS. 14-19 include a plurality of modules 1402, similar to the modules described herein. For example, each module 1402 may include a light source (e.g., light source 704-1) and a plurality of detectors (e.g., detectors 706-1 through 706-6). The wearable devices 1400 may each also include a controller (e.g., controller 112) and a processor (e.g., processor 108) and/or be communicatively connected to a controller and processor. In general, wearable device 1400 may be implemented by any suitable headgear and/or clothing article configured to be worn by a user. The headgear and/or clothing article may include batteries, cables, and/or other peripherals for the components of the optical measurement systems described herein.

Figure 14:
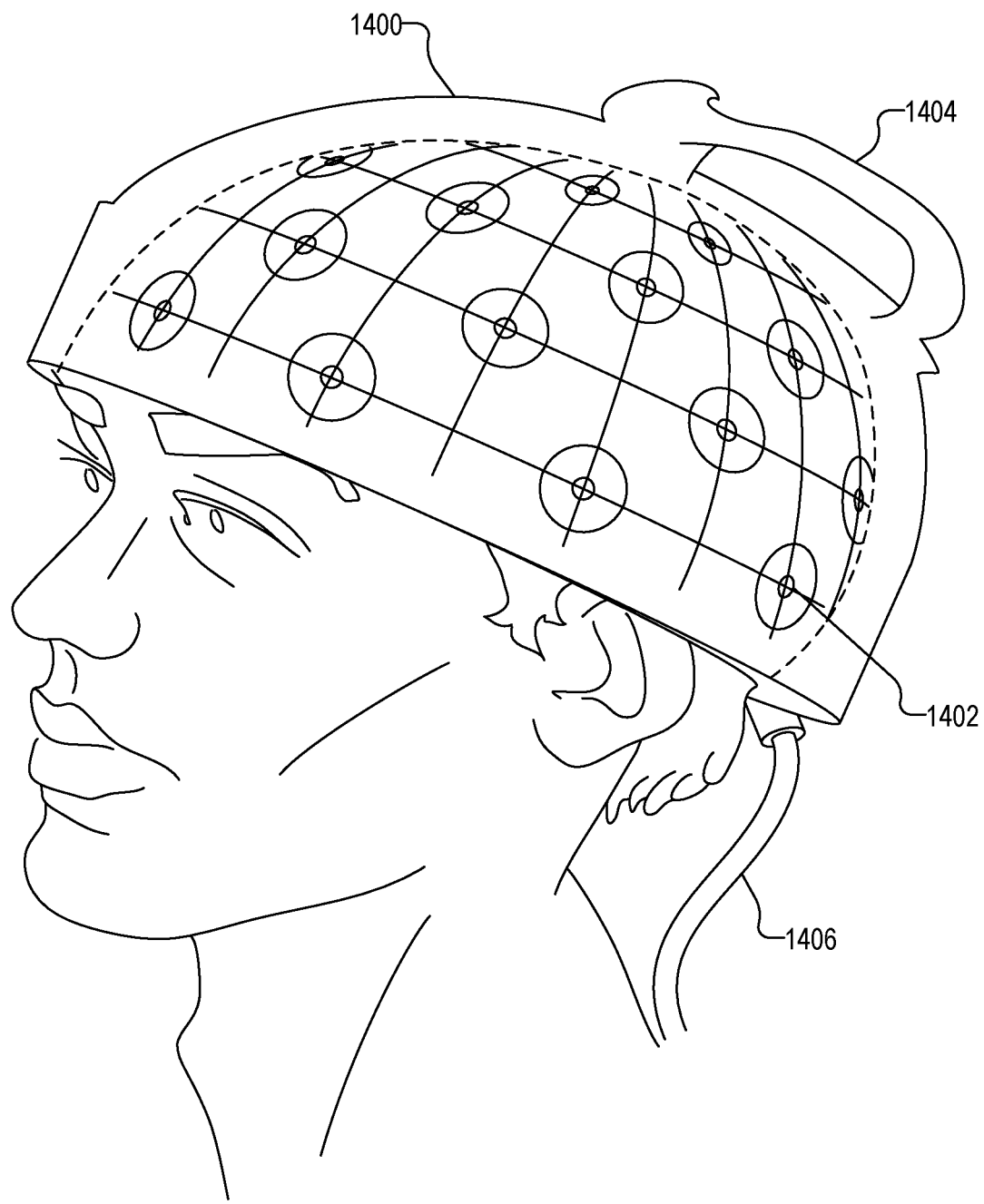
FIGS. 14-19 illustrate embodiments of a wearable device that includes elements of the optical detection systems described herein.
Figure 15:
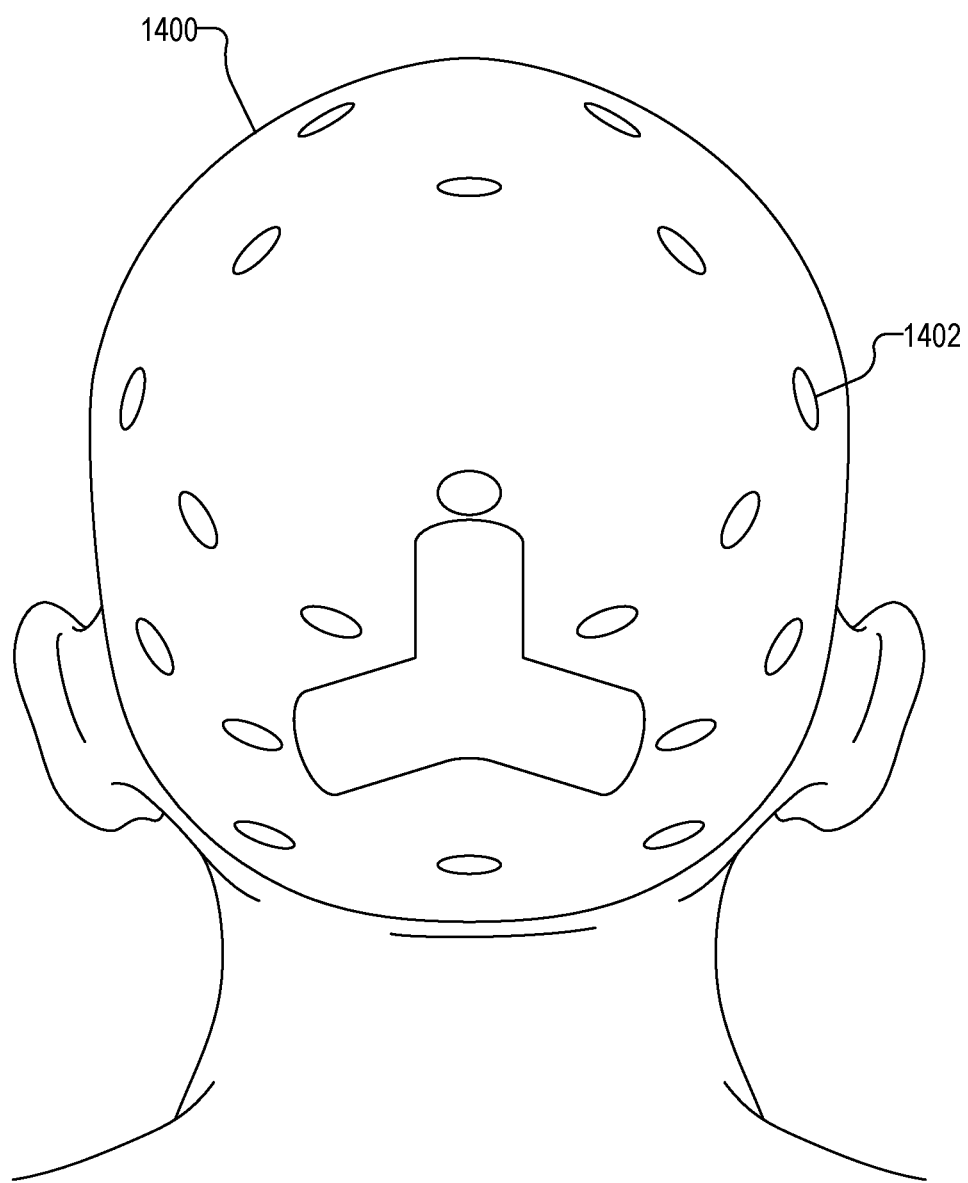
Figure 16:
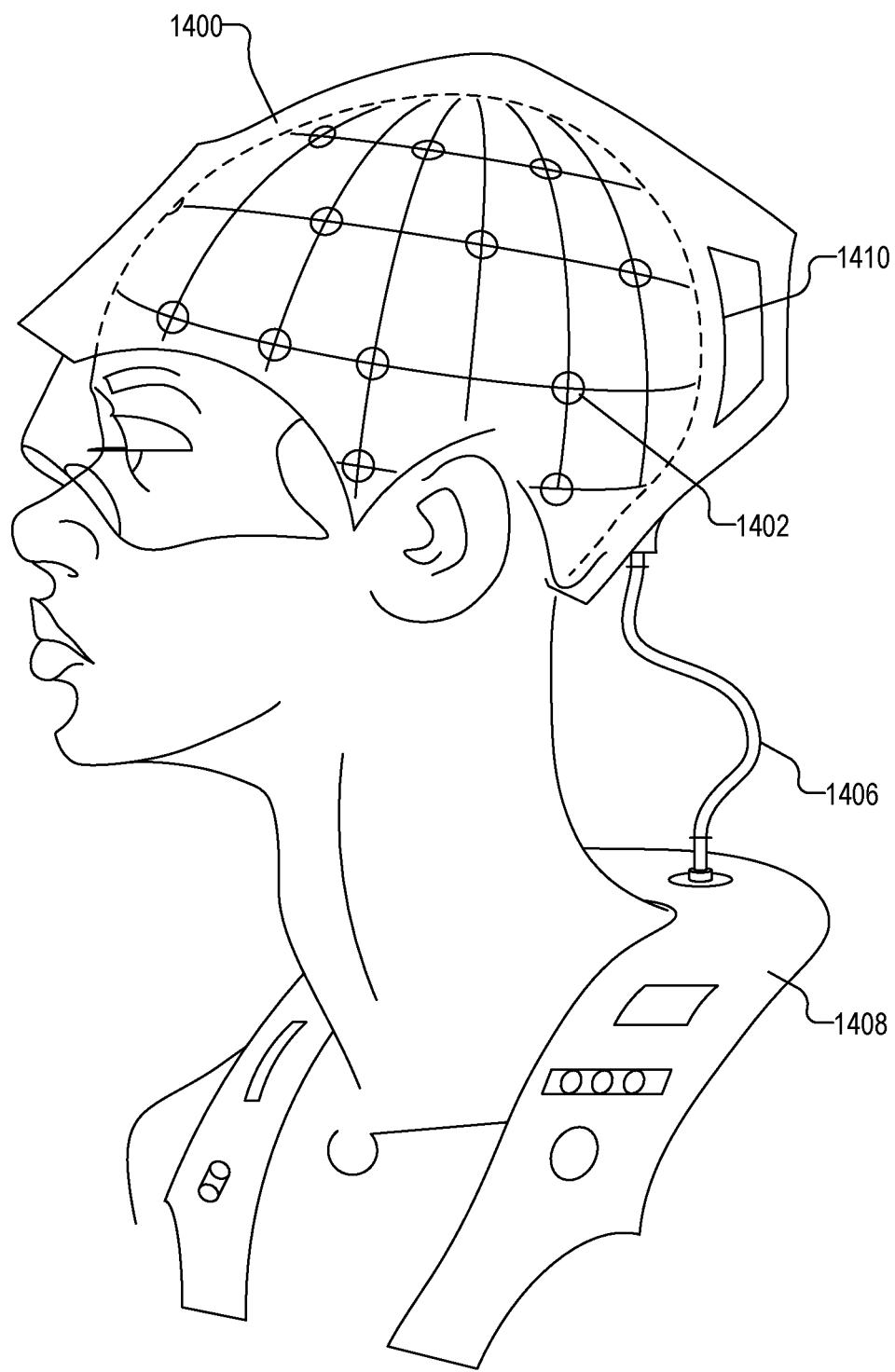

FIG. 14 illustrates an embodiment of a wearable device 1400 in the form of a helmet with a handle 1404. A cable 1406 extends from the wearable device 1400 for attachment to a battery or hub (with components such as a processor or the like). FIG. 15 illustrates another embodiment of a wearable device 1400 in the form of a helmet showing a back view. FIG. 16 illustrates a third embodiment of a wearable device 1400 in the form of a helmet with the cable 1406 leading to a wearable garment 1408 (such as a vest or partial vest) that can include a battery or a hub. Alternatively or additionally, the wearable device 1400 can include a crest 1410 or other protrusion for placement of the hub or battery.

Figure 17:
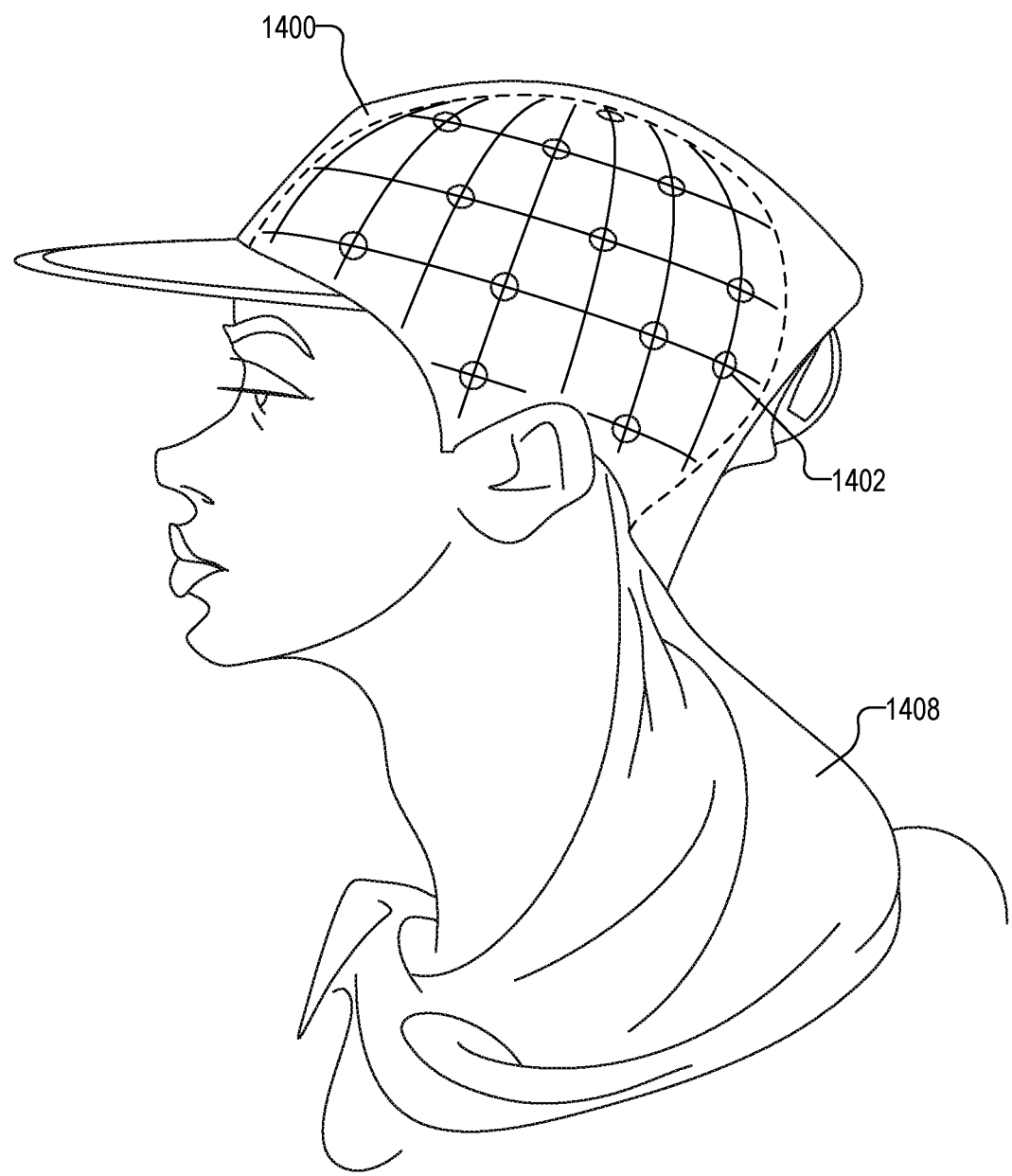
Figure 18:
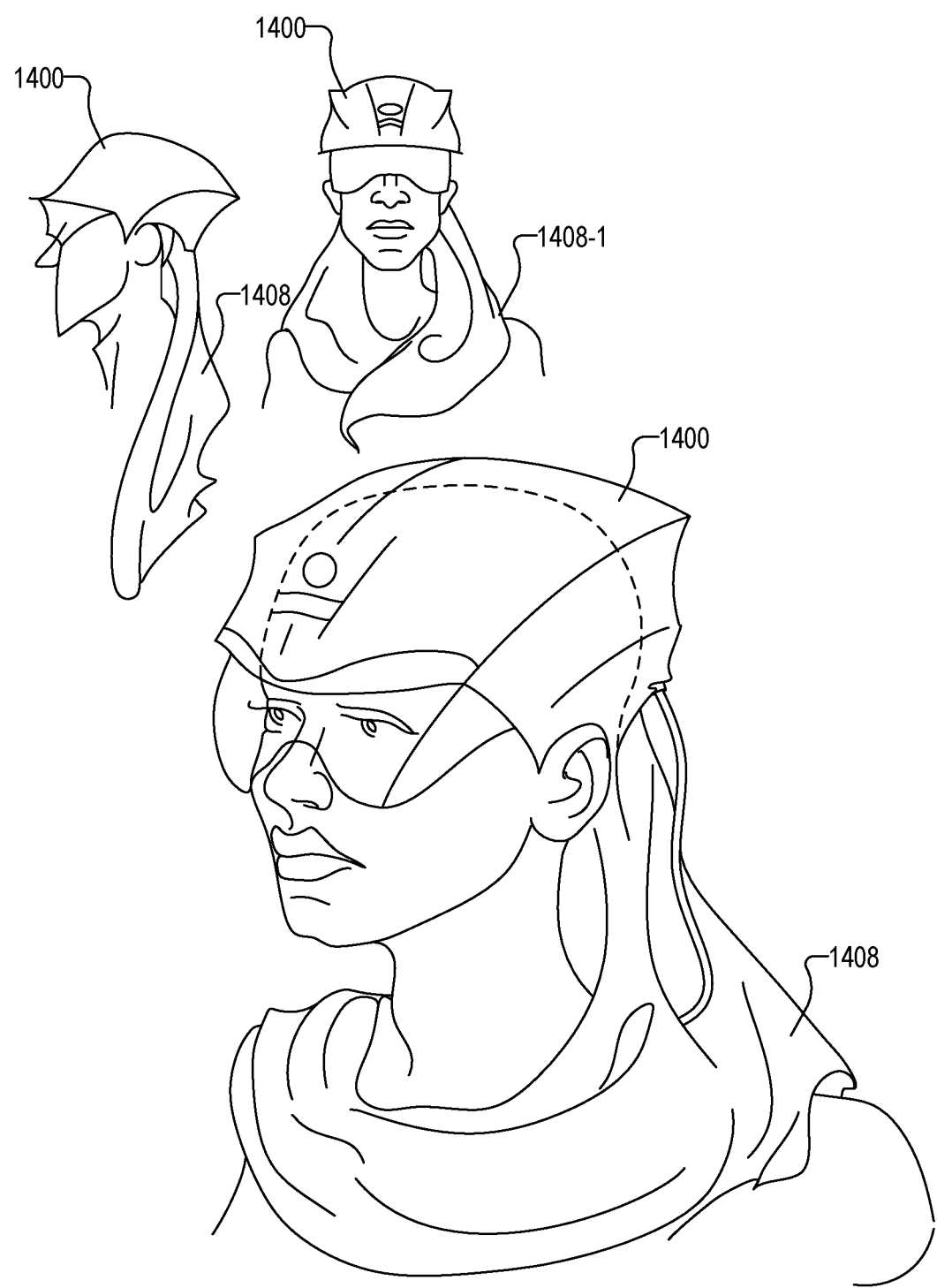
Figure 19:
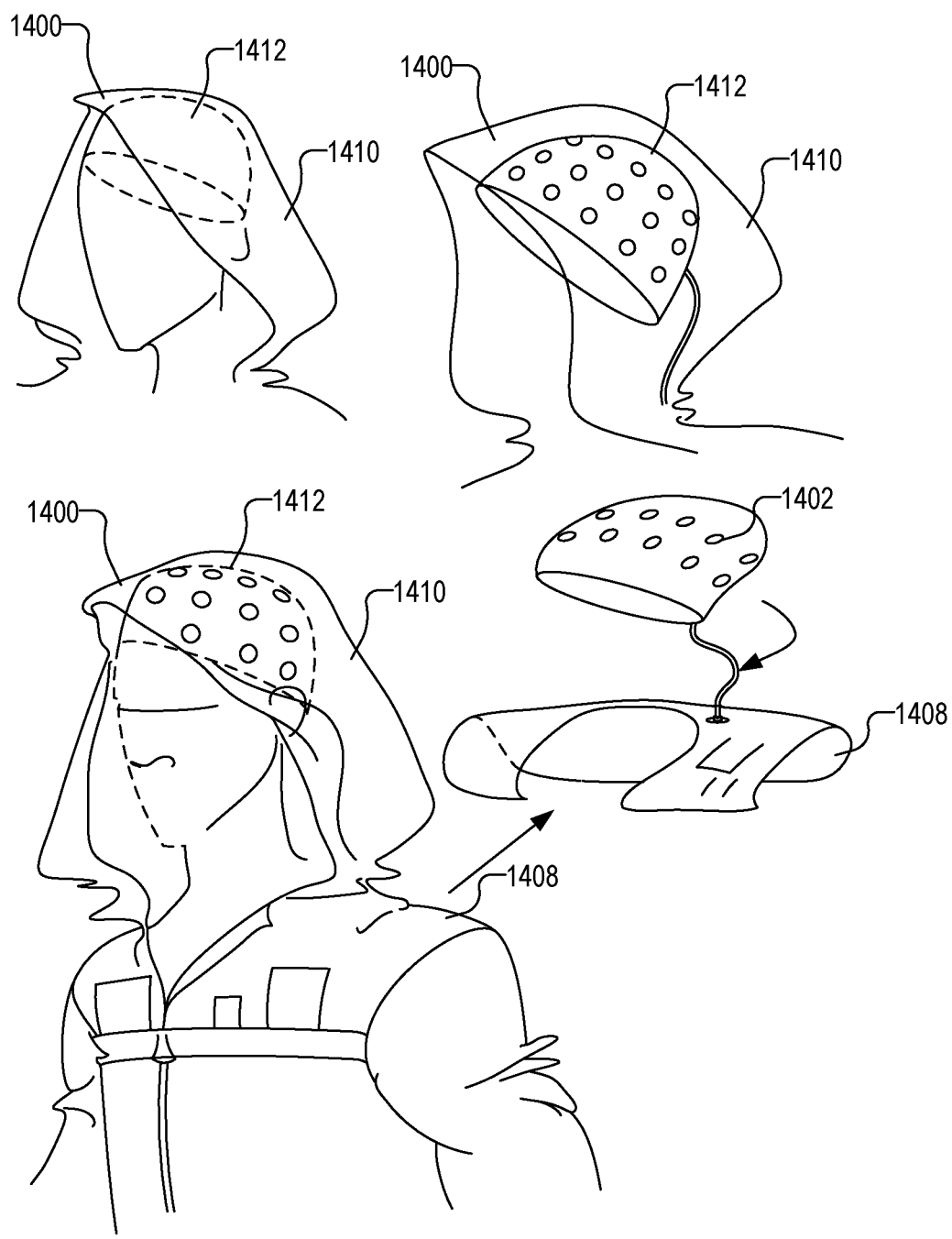

FIG. 17 illustrates another embodiment of a wearable device 1400 in the form of a cap with a wearable garment 1408 in the form of a scarf that may contain or conceal a cable, battery, and/or hub. FIG. 18 illustrates additional embodiments of a wearable device 1400 in the form of a helmet with a one-piece scarf 1408 or two-piece scarf 1408-1. FIG. 19 illustrates an embodiment of a wearable device 1400 that includes a hood 1410 and a beanie 1412 which contains the modules 1402, as well as a wearable garment 1408 that may contain a battery or hub.

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

Figure 20:
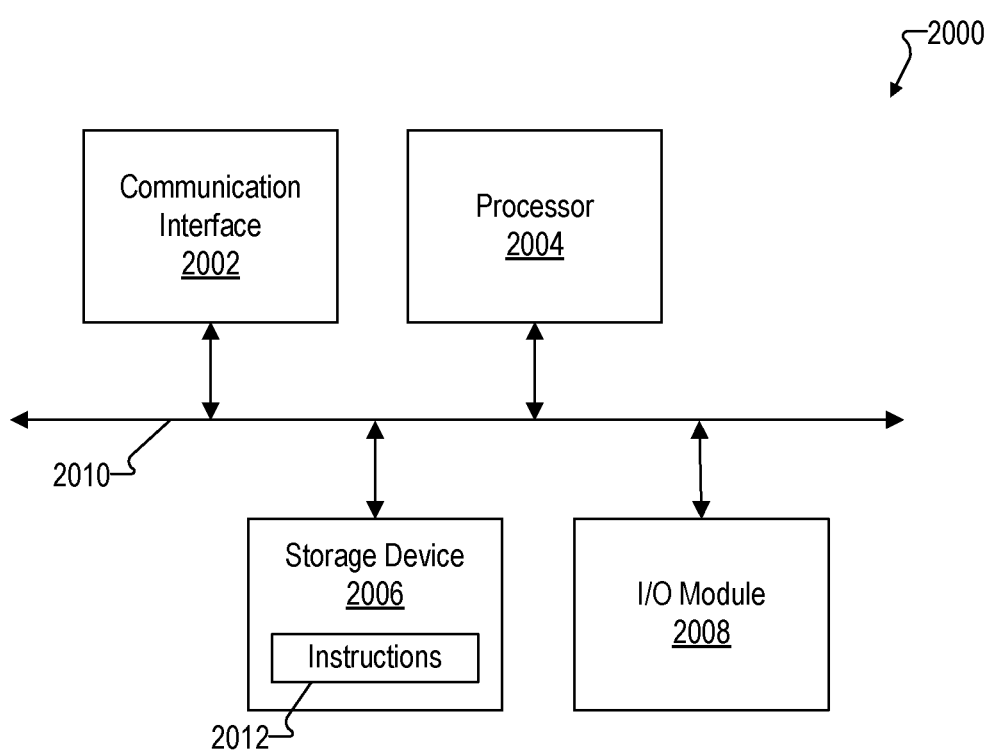
FIG. 20 illustrates an exemplary computing device.

FIG. 20 illustrates an exemplary computing device 2000 that may be specifically configured to perform one or more of the processes described herein. Any of the systems, units, computing devices, and/or other components described herein may be implemented by computing device 2000.

As shown in FIG. 20, computing device 2000 may include a communication interface 2002, a processor 2004, a storage device 2006, and an input/output ("I/O") module 2008 communicatively connected one to another via a communication infrastructure 2010. While an exemplary computing device 2000 is shown in FIG. 20, the components illustrated in FIG. 20 are not intended to be limiting. Additional or alternative components may be used in other embodiments. Components of computing device 2000 shown in FIG. 20 will now be described in additional detail.

Communication interface 2002 may be configured to communicate with one or more computing devices. Examples of communication interface 2002 include, without limitation, a wired network interface (such as a network interface card), a wireless network interface (such as a wireless network interface card), a modem, an audio/video connection, and any other suitable interface.

Processor 2004 generally represents any type or form of processing unit capable of processing data and/or interpreting, executing, and/or directing execution of one or more of the instructions, processes, and/or operations described herein. Processor 2004 may perform operations by executing computer-executable instructions 2012 (e.g., an application, software, code, and/or other executable data instance) stored in storage device 2006.

Storage device 2006 may include one or more data storage media, devices, or configurations and may employ any type, form, and combination of data storage media and/or device. For example, storage device 2006 may include, but is not limited to, any combination of the non-volatile media and/or volatile media described herein. Electronic data, including data described herein, may be temporarily and/or permanently stored in storage device 2006. For example, data representative of computer-executable instructions 2012 configured to direct processor 2004 to perform any of the operations described herein may be stored within storage device 2006. In some examples, data may be arranged in one or more databases residing within storage device 2006.

I/O module 2008 may include one or more I/O modules configured to receive user input and provide user output. I/O module 2008 may include any hardware, firmware, software, or combination thereof supportive of input and output capabilities. For example, I/O module 2008 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 2008 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 2008 is configured to provide graphical data to a display for presentation to a user. The graphical data may be representative of one or more graphical user interfaces and/or any other graphical content as may serve a particular implementation.

Figure 21:
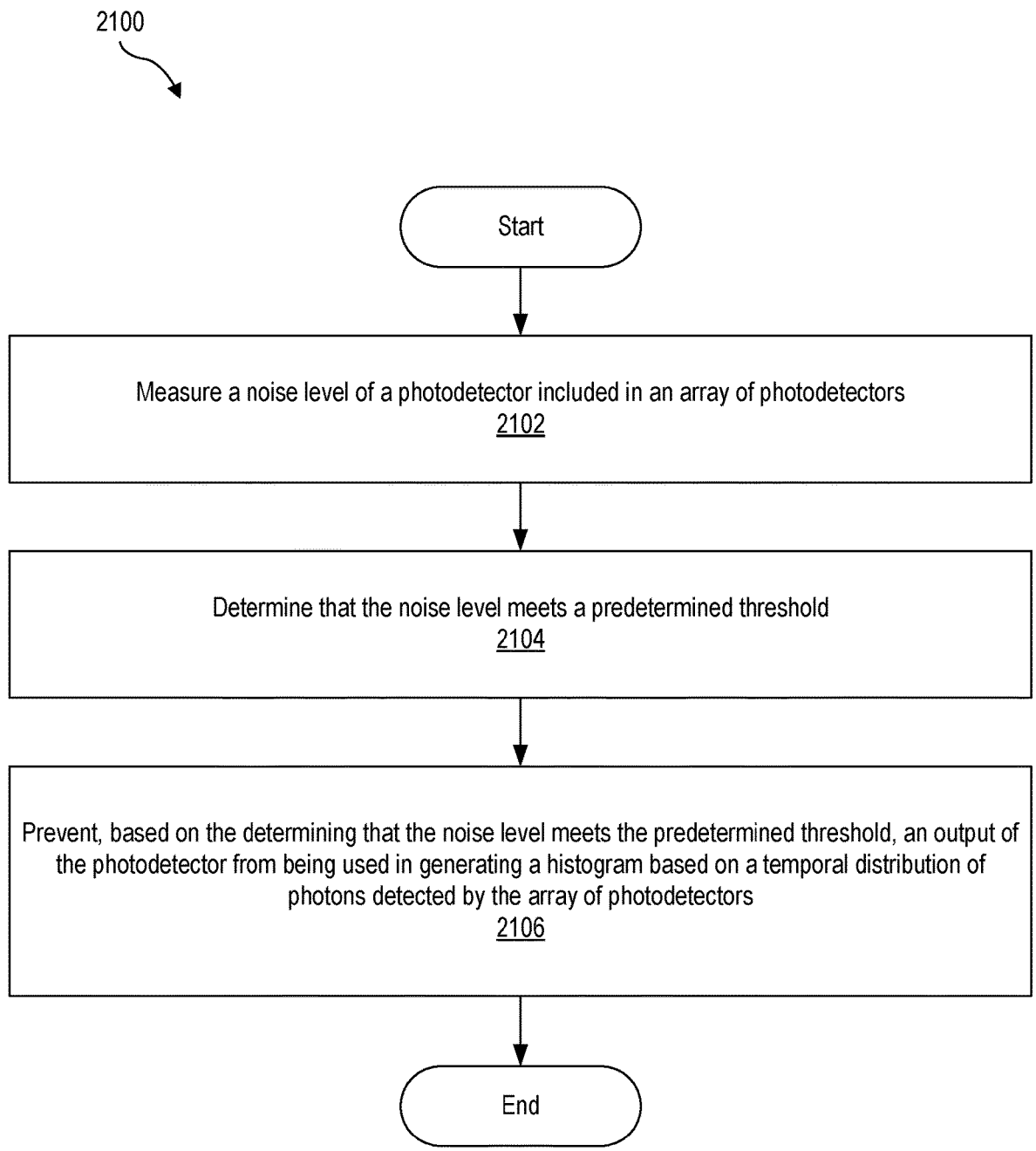
FIG. 21 illustrates an exemplary method.

FIG. 21 illustrates an exemplary method 2100 that may be performed by processing unit 906 and/or any implementation thereof. While FIG. 21 illustrates exemplary operations according to one embodiment, other embodiments may omit, add to, reorder, and/or modify any of the operations shown in FIG. 21. Each of the operations shown in FIG. 21 may be performed in any of the ways described herein.

In operation 2102, a processing unit of an optical measurement system measures a noise level of a photodetector included in an array of photodetectors.

In operation 2104, the processing unit determines that the noise level meets a predetermined threshold.

In operation 2106, the processing unit prevents, based on the determining that the noise level meets the predetermined threshold, an output of the photodetector from being used in generating a histogram based on a temporal distribution of photons detected by the array of photodetectors.

An illustrative optical measurement system includes a light source configured to emit light directed at a target, an array of photodetectors configured to detect photons of the light after the light is scattered by the target, and a processing unit. The processing unit is configured to measure a noise level of a photodetector included in the array of photodetectors and determine that the noise level meets a predetermined threshold. The processing unit is further configured to prevent, based on the determining that the noise level meets the predetermined threshold, an output of the photodetector from being used in generating a histogram based on a temporal distribution of photons detected by the array of photodetectors.

Another illustrative optical measurement system includes a wearable assembly configured to be worn by a user and including a head-mountable component configured to be attached to a head of the user. The head-mountable component includes an array of photodetectors configured to detect photons from a light pulse after the light pulse reflects off a target within the head. The wearable system further includes a processing unit. The processing unit is configured to measure a noise level of a photodetector included in the array of photodetectors and determine that the noise level meets a predetermined threshold. The processing unit is further configured to prevent, based on the determining that the noise level meets the predetermined threshold, an output of the photodetector from being used in generating a histogram based on a temporal distribution of photons detected by the array of photodetectors.

An illustrative method includes a measuring, by a processing unit, a noise level of a photodetector included in an array of photodetectors. The method further includes determining, by the processing unit, that the noise level meets a predetermined threshold. The method further includes preventing, by the processing unit, based on the determining that the noise level meets the predetermined threshold, an output of the photodetector from being used in generating a histogram based on a temporal distribution of photons detected by the array of photodetectors.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. An optical measurement system comprising:
   a light source configured to emit light directed at a target;
   an array of photodetectors configured to detect photons of the light after the light is scattered by the target; and
   a processing unit configured to:
      measure a noise level of a photodetector included in the array of photodetectors, the noise level comprising a dark count rate that measures a dark count divided by a time period;
      determine that the noise level meets a predetermined threshold comprising a dark count rate threshold; and
      prevent, based on the determining that the noise level meets the predetermined threshold, an output of the photodetector from being used in generating a histogram based on a temporal distribution of photons detected by the array of photodetectors, the preventing comprising switching the output to a monitoring circuit that monitors a characteristic of the optical measurement system separate from the photodetector.

2. The optical measurement system of claim 1, further comprising:
   a plurality of counting circuits each corresponding to a different photodetector of the array of photodetectors, the plurality of counting circuits including a counting circuit for the photodetector;
   wherein the measuring of the dark count rate of the photodetector comprises directing the counting circuit to count output signals from the photodetector during a predetermined period of time while the light source is not emitting the light.

3. The optical measurement system of claim 2, wherein the processing unit is further configured to:
   measure a dark count rate for each photodetector of the array of photodetectors using the plurality of counting circuits during the predetermined period of time; and
   prevent an output of each photodetector included in the array of photodetectors that has a dark count rate above the predetermined threshold from being used in generating the histogram.

4. The optical measurement system of claim 3, further comprising:
   a one-time programmable memory configured to store data representative of each photodetector having a dark count rate that is above the predetermined threshold;

wherein the processing unit is further configured to periodically measure the dark count rate for each photodetector not represented in the one-time programmable memory as having the dark count rate that is above the predetermined threshold.

5. The optical measurement system of claim 1, wherein the measuring of the noise level of the photodetector comprises measuring a signal-to-noise ratio (SNR) of the photodetector.

6. The optical measurement system of claim 5, further comprising a plurality of counting circuits each corresponding to a different photodetector of the array of photodetectors, the plurality of counting circuits including a counting circuit for the photodetector;
wherein the measuring of the SNR of the photodetector comprises directing the counting circuit to:
count output signals from the photodetector for a first predetermined period of time while the light source is not emitting light, and
count output signals from the photodetector for a second predetermined period of time while the light source is emitting a uniform light.

7. The optical measurement system of claim 6, wherein the determining that the noise level meets the predetermined threshold comprises determining that the SNR is below the predetermined threshold.

8. The optical measurement system of claim 6, wherein the processing unit is further configured to:
measure an SNR for each photodetector of the array of photodetectors using the plurality of counting circuits during the first and second predetermined periods of time; and
prevent an output of each photodetector included in the array of photodetectors that has an SNR below the predetermined threshold from being used in generating the histogram.

9. The optical measurement system of claim 8, wherein the preventing the output of each photodetector included in the array of photodetectors that has an SNR below the predetermined threshold from being used in generating the histogram comprises switching the output of each photodetector included in the array of photodetectors that has an SNR below the predetermined threshold to the monitoring circuit.

10. The optical measurement system of claim 1, wherein the monitoring circuit is configured to determine a temperature associated with the optical measurement system based on the noise level of the photodetector.

11. The optical measurement system of claim 1, wherein the monitoring circuit is configured to determine a peak location of a light pulse emitted by the light source.

12. The optical measurement system of claim 1, wherein the monitoring circuit is configured to determine an excess bias voltage of the photodetector.

13. The optical measurement system of claim 1, wherein each photodetector of the array of photodetectors comprises:
a single photon avalanche diode (SPAD); and
a fast gating circuit configured to arm and disarm the SPAD.

14. The optical measurement system of claim 1, wherein the array of photodetectors is included in a wearable device configured to be worn by a user.

15. The optical measurement system of claim 14, wherein the wearable device includes a head-mountable component configured to be worn on a head of a user.

16. A method comprising:
measuring a noise level of a photodetector of an optical measurement system, the noise level comprising a dark count rate that measures a dark count divided by a time period;
determining that the noise level meets a predetermined threshold comprising a dark count rate threshold; and
preventing, based on the determining that the noise level meets the predetermined threshold, an output of the photodetector from being used to determine a histogram based on a temporal distribution of photons detected by an array of photodetectors, the preventing comprising switching the output to a monitoring circuit that monitors a characteristic of the optical measurement system separate from the photodetector.

17. The method of claim 16, further comprising:
measuring a dark count rate for each photodetector of the array of photodetectors using a plurality of counting circuits during the predetermined period of time; and
preventing an output of each photodetector included in the array of photodetectors that has a dark count rate above the predetermined threshold from being used in generating the histogram.

18. The method of claim 17, further comprising:
measuring, periodically, the dark count rate for each photodetector not represented in a one-time programmable memory as having the dark count rate that is above the predetermined threshold, the one-time programmable memory configured to store data representative of each photodetector having a dark count rate that is above the predetermined threshold.

19. The method of claim 17, wherein the preventing the output of each photodetector included in the array of photodetectors that has a dark count rate above the predetermined threshold from being used in generating the histogram comprises switching the output of each photodetector included in the array of photodetectors that has a dark count rate above the predetermined threshold to the monitoring circuit.

20. The method of claim 16, wherein the monitoring circuit is configured to determine a temperature associated with the optical measurement system based on the noise level of the photodetector.

* * * * *